US010835323B2

(12) United States Patent
Leong et al.

(10) Patent No.: US 10,835,323 B2
(45) Date of Patent: Nov. 17, 2020

(54) SYSTEM AND APPARATUS FOR GUIDING AN INSTRUMENT

(71) Applicants: Institute of Technical Education, Singapore (SG); National University Hospital (Singapore) Pte Ltd., Singapore (SG); National University of Singapore, Singapore (SG)

(72) Inventors: Foo Soo Leong, Singapore (SG); Ng Ka Wei, Singapore (SG); Goh Jin Quan, Singapore (SG); Ting Poh Hua, Singapore (SG); Lee Teck Kheng, Singapore (SG); Wu Qinghui, Singapore (SG); Chiong Edmund, Singapore (SG); Esuvaranathan Kesavan, Singapore (SG)

(73) Assignees: Institute of Technical Education, Singapore (SG); National University Hospital (Singapore) Pte Ltd., Singapore (SG); National University of Singapore, Singapore (SG)

( * ) Notice: Subject to any disclaimer, the term of this patent is extended or adjusted under 35 U.S.C. 154(b) by 1218 days.

(21) Appl. No.: 14/915,112

(22) PCT Filed: Aug. 28, 2013

(86) PCT No.: PCT/SG2013/000375
§ 371 (c)(1),
(2) Date: Feb. 26, 2016

(87) PCT Pub. No.: WO2015/030671
PCT Pub. Date: Mar. 5, 2015

(65) Prior Publication Data
US 2016/0206383 A1    Jul. 21, 2016

(51) Int. Cl.
*A61B 34/20* (2016.01)
*A61B 90/11* (2016.01)
(Continued)

(52) U.S. Cl.
CPC .............. *A61B 34/20* (2016.02); *A61B 90/11* (2016.02); *A61B 2017/00911* (2013.01);
(Continued)

(58) Field of Classification Search
CPC .............. A61B 34/20; A61B 2034/302; A61B 2034/305; A61B 2034/2055;
(Continued)

(56) References Cited

U.S. PATENT DOCUMENTS 4,461,284 A * 7/1984 Fackler .................. A61B 17/02
248/288.51
4,485,453 A * 11/1984 Taylor ...................... B25J 9/026
318/568.1
(Continued)

FOREIGN PATENT DOCUMENTS

WO    WO2008/070685 A2    6/2008
WO    WO2009/104853 A1    8/2009

*Primary Examiner* — Julian W Woo
(74) *Attorney, Agent, or Firm* — Kilpatrick Townsend & Stockton LLP

(57) ABSTRACT

A system and an apparatus for guiding an instrument may be provided, the apparatus comprising a main body; a holding member for holding an instrument, the holding member coupled to the main body; and one or more actuating members configured to effect movement of the holding member such that said movement of the holding member is capable of providing rotational movement of an instrument about a pivot point external the apparatus. The holding member may preferably be configured to co-operate with a compliance device, said compliance device capable of holding the instrument.

38 Claims, 31 Drawing Sheets

(51) Int. Cl.
  *A61B 34/30* (2016.01)
  *A61B 17/34* (2006.01)
  *A61B 17/00* (2006.01)
  *A61B 90/57* (2016.01)
(52) U.S. Cl.
  CPC .............. *A61B 2017/00915* (2013.01); *A61B 2017/3405* (2013.01); *A61B 2017/3409* (2013.01); *A61B 2034/2055* (2016.02); *A61B 2034/302* (2016.02); *A61B 2034/305* (2016.02); *A61B 2090/571* (2016.02)
(58) Field of Classification Search
  CPC .............. A61B 2090/571; A61B 90/11; A61B 2017/00911; A61B 2017/00915; A61B 2017/3405; A61B 2017/3409
  See application file for complete search history.

(56) References Cited

U.S. PATENT DOCUMENTS

| | | | | |
|---|---|---|---|---|
| 4,979,093 | A * | 12/1990 | Laine | B23Q 1/25 700/61 |
| 5,142,930 | A * | 9/1992 | Allen | A61B 6/12 414/4 |
| 5,170,790 | A * | 12/1992 | Lacoste | A61B 8/12 128/122.1 |
| 5,402,801 | A * | 4/1995 | Taylor | A61B 34/20 128/898 |
| 5,776,144 | A * | 7/1998 | Leysieffer | A61F 11/004 600/25 |
| 6,106,511 | A * | 8/2000 | Jensen | B25J 9/1065 600/102 |
| 6,264,396 | B1 * | 7/2001 | Dobrovolny | A61B 17/0206 403/384 |
| 6,514,239 | B2 * | 2/2003 | Shimmura | A61B 90/50 600/427 |
| 6,702,805 | B1 * | 3/2004 | Stuart | B25J 9/1065 600/102 |
| 6,723,106 | B1 * | 4/2004 | Charles | B25J 9/1065 606/130 |
| 6,758,843 | B2 * | 7/2004 | Jensen | B25J 9/1065 600/102 |
| 7,556,626 | B2 * | 7/2009 | Ueda | A61B 90/50 600/102 |
| 7,803,163 | B2 * | 9/2010 | Skakoon | A61B 90/11 606/130 |
| 8,183,469 | B2 * | 5/2012 | Sunohara | H05K 3/4092 174/267 |
| 8,992,564 | B2 * | 3/2015 | Jaspers | A61B 34/70 606/205 |
| 9,532,837 | B2 * | 1/2017 | Singh | A61B 90/10 |
| 10,278,781 | B2 * | 5/2019 | Taylor | B25J 15/0466 |
| 10,322,514 | B2 * | 6/2019 | Vander Poorten | A61B 34/30 |
| 2005/0234435 | A1 | 10/2005 | Layer | |
| 2008/0058776 | A1 | 3/2008 | Jo et al. | |
| 2009/0326322 | A1 | 12/2009 | Diolaiti | |
| 2010/0234856 | A1 | 9/2010 | Stoianovici et al. | |
| 2011/0277775 | A1 | 11/2011 | Holop et al. | |

* cited by examiner

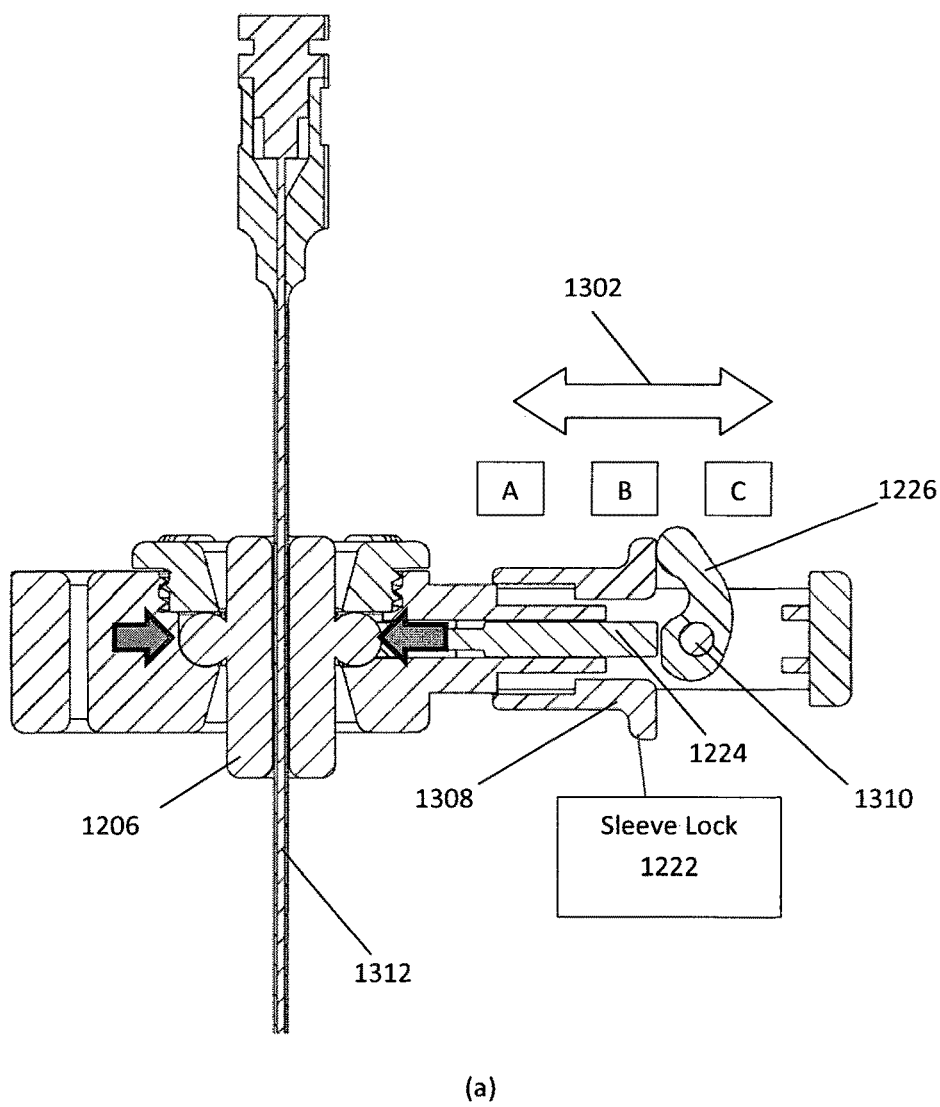
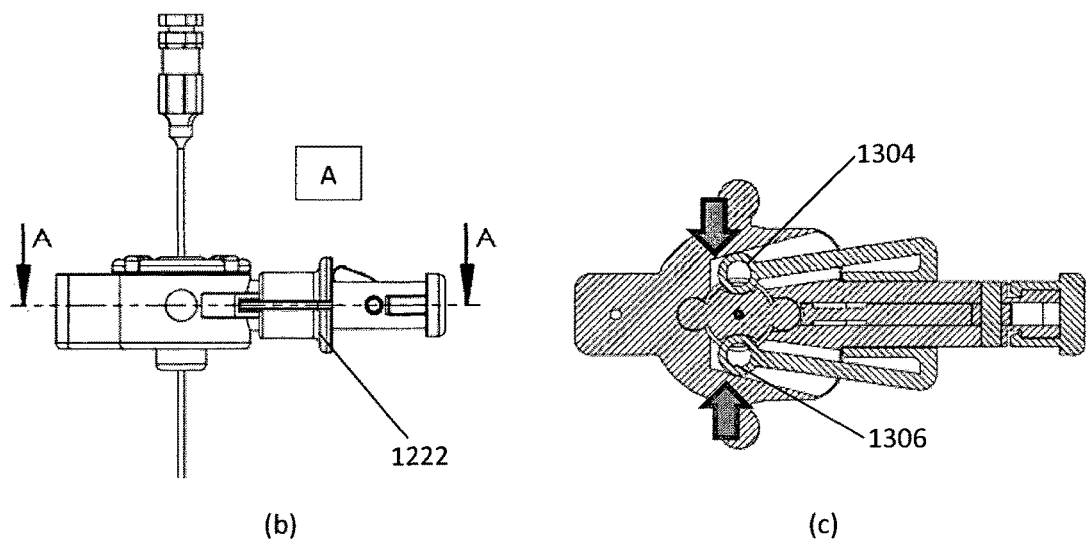
Figure 13

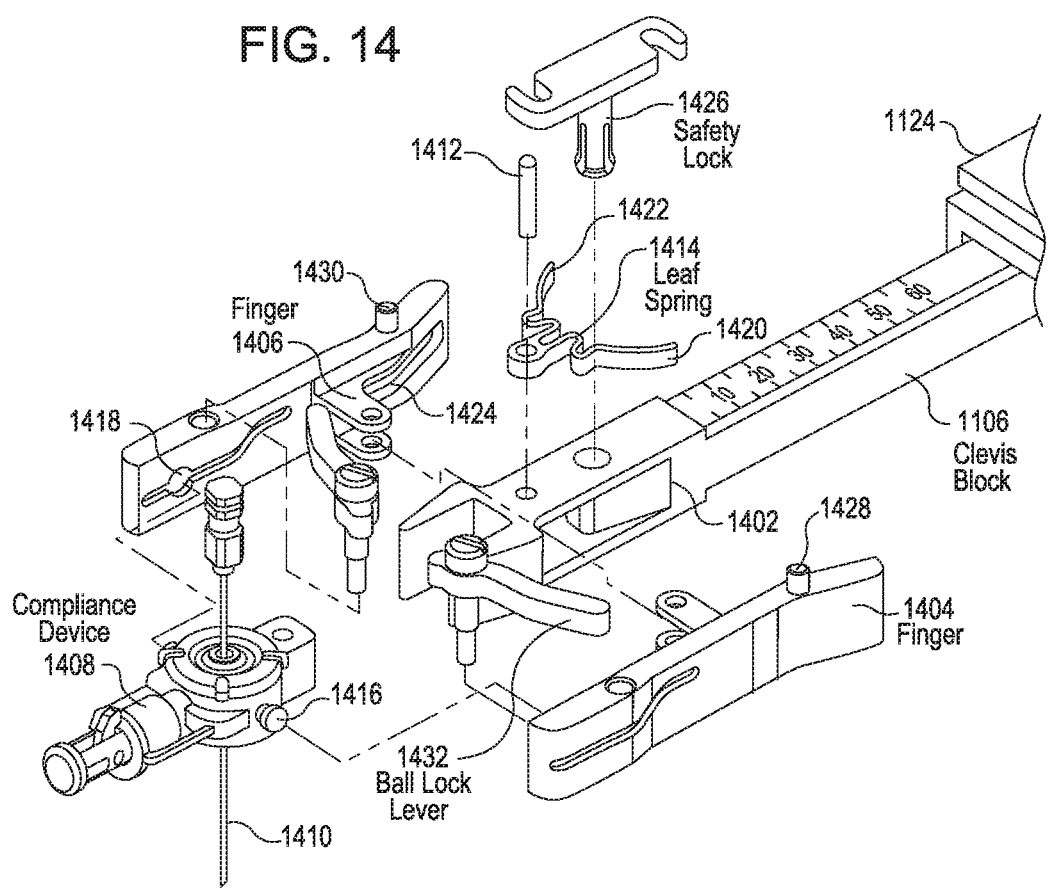

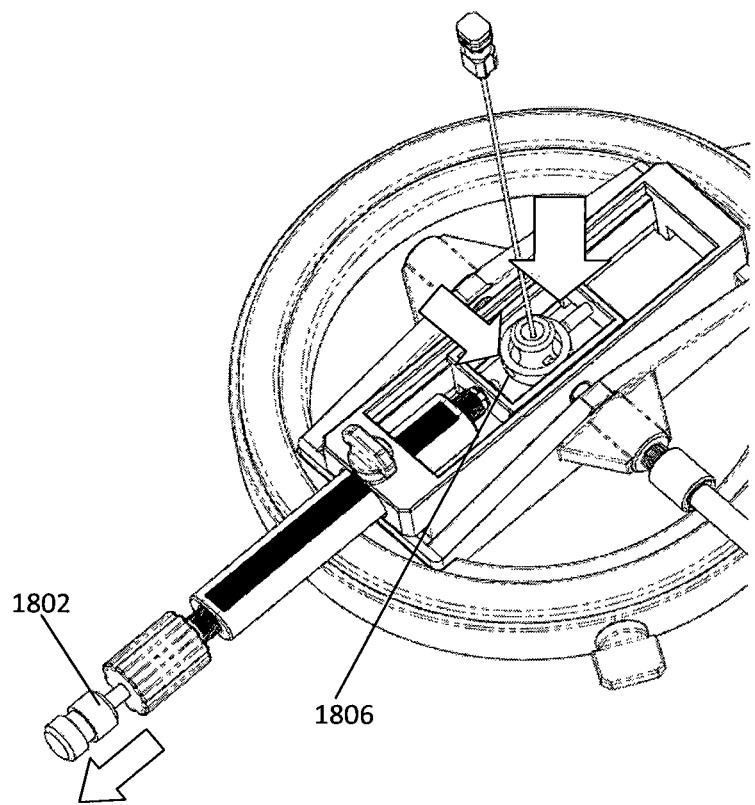
(c)
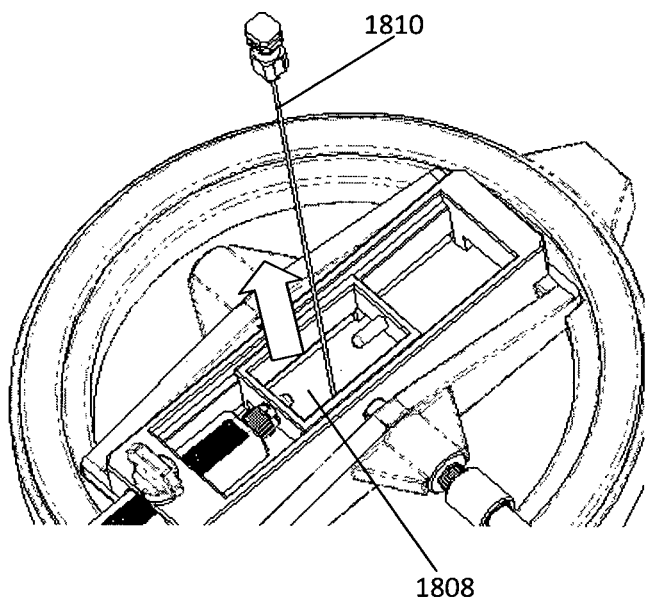
(d)
Figure 18

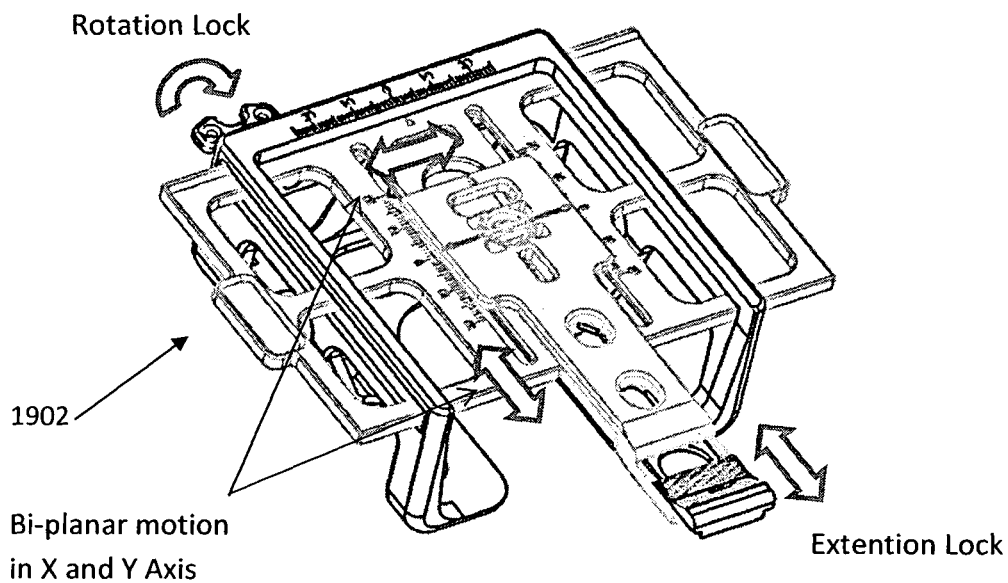
(a)
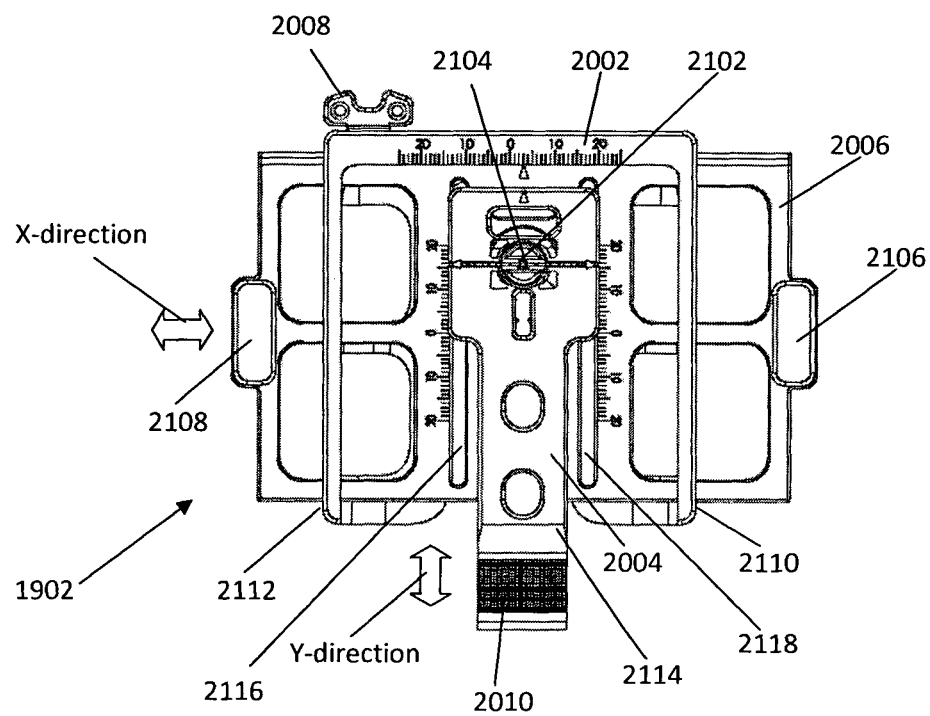
(b)
Figure 21

(a) (b)

SYSTEM AND APPARATUS FOR GUIDING AN INSTRUMENT

TECHNICAL FIELD

The present disclosure relates broadly to a system and to an apparatus for guiding an instrument.

BACKGROUND

With the use of current technologies, minimally invasive techniques/procedures are desired for accessing parts of subjects. For example, percutaneous access to the kidney (PAK) is a minimally invasive procedure to create renal access in kidney stones removal. PAK typically uses a hollow needle to puncture the skin of a subject, and is inserted in a substantially precise manner into the pelvicalyceal system of the subject containing the kidney stone target. Thereafter, a guide wire is inserted through the hollow needle, and the wire guides the insertion of endoscopic surgical instruments that can fragment and remove the stone(s). Typically, the techniques, such as the PAK process, are aided using radioactive imaging e.g. x-ray etc. For example, the PAK process typically uses a C-arm fluoroscopy throughout the process to locate the target.

While it has been recognised that minimally invasive techniques offer benefits such as less pain, smaller scars, less risk of infection and faster recovery, as compared to open incisions, it has also been recognised that such invasive techniques are typically difficult to perform. For example, PAK is typically a significantly complicated stone removal technique to master due to a steep learning curve. The insertion process in PAK is significantly dependent on the experience of the surgeon to manipulate and align the needle. It is recognised that the tedious and time consuming part of the PAK procedure is the alignment and manipulation of the needle.

Furthermore, prolonged procedural time during usage of minimally invasive techniques typically increases the risk of perioperative complications of subjects. In addition, prolonged procedural time typically increases the health risk of surgical crews due to exposure to radioactive imaging e.g. x-ray etc. Furthermore, it has been recognised that prolonged procedural time imposes a burden on hospitals given that operating theatres are typically in constant demand.

In view of the challenges facing techniques such as PAK procedures, robotic systems are being developed to facilitate such procedures. For example, a fully automated robotic system aided by image guiding system and motorised needle insertion driver (PAKY-RCM) is currently in development.

However, the inventors have recognised that there are a number of limitations associated with robot-assisted percutaneous renal access (PAKY). For example, one limitation is related to kidney movement within the retro-peritoneum during respiratory variation or subject movement. Robotic systems are typically unable to adjust to a target which is moved due to e.g. breathing motions. Another exemplary limitation is related to the various tissue interfaces that a needle typically traverses prior to reaching the target. Robotic systems are typically unable to adjust to minute deviations of the needle path due to the needle meeting resistance in the tissue interfaces, and the accumulation of minute deviations can cause a target to be missed, unless a surgeon's intervention is introduced. Furthermore, it has been found that robotic systems can cause undesirable shadowing effects for radioactive imaging performed for monitoring e.g. the target or the progress of the process. In addition, the cost of implementing a robotic system is significantly high. In addition, surgeons may prefer a manual method over a robotic system because tactile feedback during insertion can be useful information on whether the target has been reached. Thus, typically, an access method under the control of a surgeon can provide a lower cost and may be more preferred.

Hence, in view of the above, there exists a need for a system and an apparatus for guiding an instrument that seek to address at least one of the above problems.

SUMMARY

In accordance with a first aspect, there is provided an apparatus for guiding an instrument, the apparatus comprising, a main body; a holding member for holding an instrument, the holding member coupled to the main body; and one or more actuating members configured to effect movement of the holding member such that said movement of the holding member is capable of providing rotational movement of an instrument about a pivot point external the apparatus.

The apparatus may further comprise the one or more actuating members being configured to effect the movement as translational movements within a plane that is parallel to a plane horizontal with respect to the main body.

Each actuating member may be provided for effecting the translational movement of the holding member along a respective axis within the plane.

The apparatus may further comprise an extendable member coupled to the main body, the extendable member capable of offsetting a position of the holding member from the main body.

The holding member may comprise at least one clamping finger being urged towards another clamping finger.

The at least one clamping finger may comprise an end portion for a force to be applied to, for release of the instrument from the apparatus.

The apparatus may further comprise a lock member for engaging the clamping fingers to restrict movement of the at least one clamping finger.

The holding member may be configured to co-operate with a compliance device, said compliance device capable of holding the instrument.

The compliance device may comprise two or more spherical joints that allow the compliance device to be compliant to movement along two perpendicular axes, and the compliance device may further comprise a plunger assembly for restricting movement of the instrument.

The compliance device may be capable of being individually locked in movement along each axis.

The compliance device may be constructed of a material to substantially prevent shadowing effects of the compliance device in an imaging procedure.

The material may be at least one selected from the group consisting of titanium, glass, polystyrene, polyurethane, PVC, polyether ether ketone (PEEK) and paper.

The holding member may comprise an extendable shaft.

The holding member may be configured to co-operate with a compliance device, said compliance device capable of holding the instrument.

The compliance device may be configured to be contacted by at least two rounded walls provided on the main body of the apparatus that allow the compliance device to be compliant to movement along at least one axis.

The holding member may further comprise a plug that is capable of actuating the extendable shaft for engagement with the compliance device, the extending or retracting of the shaft for respectively release or maintaining the compliance device in relation to the main body.

The compliance device may be constructed of a material to substantially prevent shadowing effects of the compliance device in an imaging procedure.

The material is at least one selected from the group consisting of titanium, glass, polystyrene, polyurethane, PVC, polyether ether ketone (PEEK) and paper.

The apparatus may further comprise a mounting base disposed on the main body, the mounting base for contacting a subject surface such that the holding member is disposed at a distance from the subject surface.

The mounting base may comprise two or more mounting segments for contacting the subject surface.

A first actuating member may comprise one or more guiding slots and a second actuating member may be capable of moving in relation to the first actuating member via the guiding slots.

The first actuating member may further comprise a travel path such that said providing rotational movement of an instrument about a pivot point external the apparatus may be within the travel path.

The apparatus may further comprise a locking latch member that is capable of causing extension of one or more locking sub-members to engage one or more walls of the travel path, to restrict movement of the holding member in relation to the travel path.

At least one actuating member may be provided with a pre-determined weakened portion such that said at least one actuating member is breakable for releasing an instrument from the holding member.

The one or more actuating members may comprise a hand-operable slider mechanism.

The apparatus may further comprise a rotation member coupled to the main body for effecting rotation of the main body about a vertical axis passing through a center of the main body.

The apparatus may further comprise a rotational locking member for restricting rotation of the main body.

The apparatus may further comprise a locking member capable of restricting movement of the holding member such that only further movement of the holding member along a single axis is allowed.

At least the holding member may be constructed of a material to substantially prevent shadowing effects of the holding member in an imaging procedure.

The material is at least one selected from the group consisting of titanium, glass, polystyrene, polyurethane, PVC, polyether ether ketone (PEEK) and paper.

In accordance with a second aspect, there is provided a system for guiding an instrument, the system comprising an imaging device having an imaging surface; a visual alignment module, the visual alignment module comprising: a visible light source; a refraction/reflection member for receiving light from the visible light source, the refraction/reflection member being substantially transparent to the imaging device and being disposed in an imaging path of the imaging device; and wherein the visible light source is disposed offset from the imaging path of the imaging device such that a visible reference of the imaging path and being perpendicular to the imaging surface is capable of being provided by the refraction/reflection member.

The visual alignment module may be movable such that the visible light source is adjustable within a plane parallel to a plane of the imaging surface.

The system may further comprise an apparatus of a first aspect and/or mentioned above, and wherein an instrument may be capable of being guided according to the visible reference.

In accordance with a third aspect, there is provided a method for providing a visible reference to guide an instrument, the method comprising providing an imaging device capable of imaging a target; providing a visual alignment module, the visual alignment module comprising: a visible light source; a refraction/reflection member for receiving light from the visible light source, the refraction/reflection member being substantially transparent to the imaging device and being disposed in an imaging path of the imaging device; wherein the visible light source is disposed offset from the imaging path of the imaging device; using the refraction/reflection member to provide a visible reference of the imaging path; and guiding the instrument into the imaging path based on the visible reference.

For the step of guiding the instrument, the method may further comprise using the imaging device to image the instrument position.

In accordance with a fourth aspect, there is provided a method for guiding an instrument, the method comprising holding an instrument using an apparatus; providing a pivot point external the apparatus; actuating one or more actuating members of the apparatus to move the instrument so as to provide rotational movement of the instrument about the pivot point external the apparatus.

For the step of actuating one or more actuating members to move the instrument, the method may further comprise effecting the movement of the instrument in a translational manner within a plane that is parallel to a plane horizontal with respect to a main body of the apparatus.

For the step of actuating one or more actuating members to move the instrument, the method may further comprise effecting the movement of the instrument along a respective axis of each actuating member within the plane.

BRIEF DESCRIPTION OF THE DRAWINGS

Example embodiments of the invention will be better understood and readily apparent to one of ordinary skill in the art from the following written description, by way of example only, and in conjunction with the drawings, in which:

FIG. 14 is an exploded view of a clamping mechanism/device of the apparatus of FIG. 11.

FIG. 21(a) is a schematic drawing of the apparatus of FIG. 19 when assembled.

FIG. 21(b) is a schematic top view drawing of the apparatus of FIG. 21(a).

DETAILED DESCRIPTION

Figure 1A:
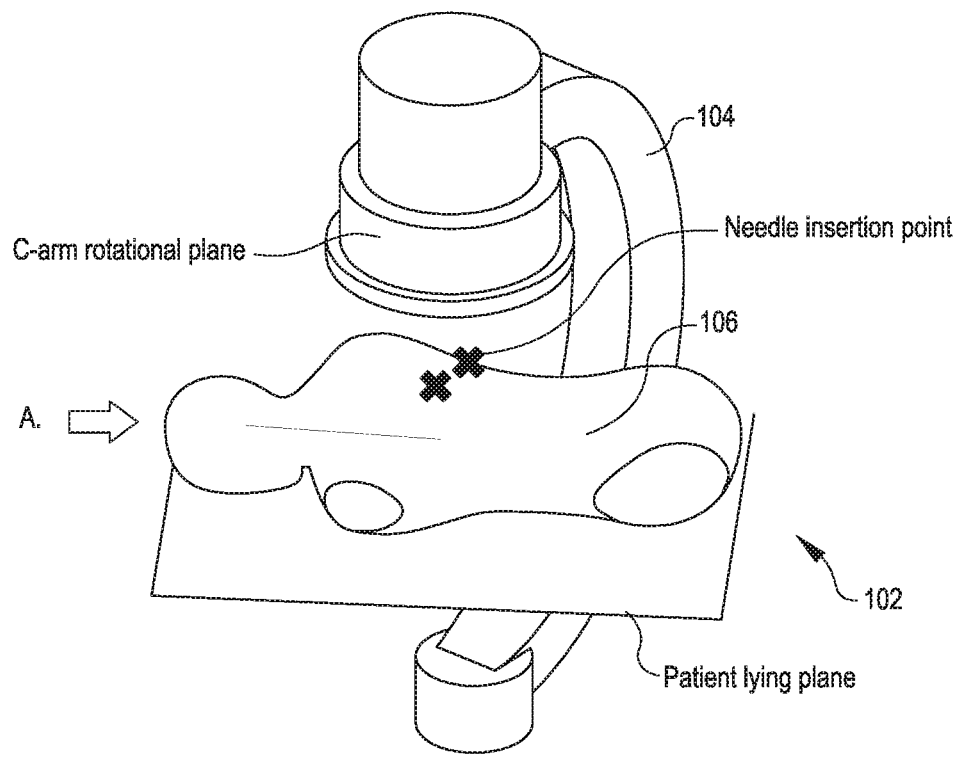
FIG. 1(a) is a schematic drawing illustrating a system for guiding an instrument in an example embodiment.

Example embodiments described herein may provide a system for guiding an instrument and an apparatus for guiding an instrument. The instrument may be, but is not limited to, a needle. The needle may be, but is not limited to, a hollow needle e.g. for introduction of equipment through the hollow needle. The system and apparatus may be used for, but is not limited to, percutaneous access to the kidney (PAK) procedures. The system and apparatus may result in a passive PAK assist device (PAK-AD) for assisting a user during operative procedures.

The terms "coupled" or "connected" as used in this description are intended to cover both directly connected or connected through one or more intermediate means, unless otherwise stated.

Additionally, when describing some embodiments, the disclosure may have disclosed a method and/or process as a particular sequence of steps. However, unless otherwise required, it will be appreciated the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

In the description herein, references to "tilting" movement, and "rotational" (or rotation) movement about a pivot point, of an instrument are used interchangeably. It is appreciated that the instrument is caused to move or moved to a sloping/inclined position with respect to a starting position of the instrument.

FIG. 1(a) is a schematic drawing illustrating a system 102 for guiding an instrument in an example embodiment. An imaging structure 104 is provided for facilitating imaging of a subject 106. In the example embodiment, the imaging structure 104 is preferably a so-called C-arm. The C-arm 104 is capable of rotating in a substantially circular manner about an axis passing through arrow A.

Figure 1B:
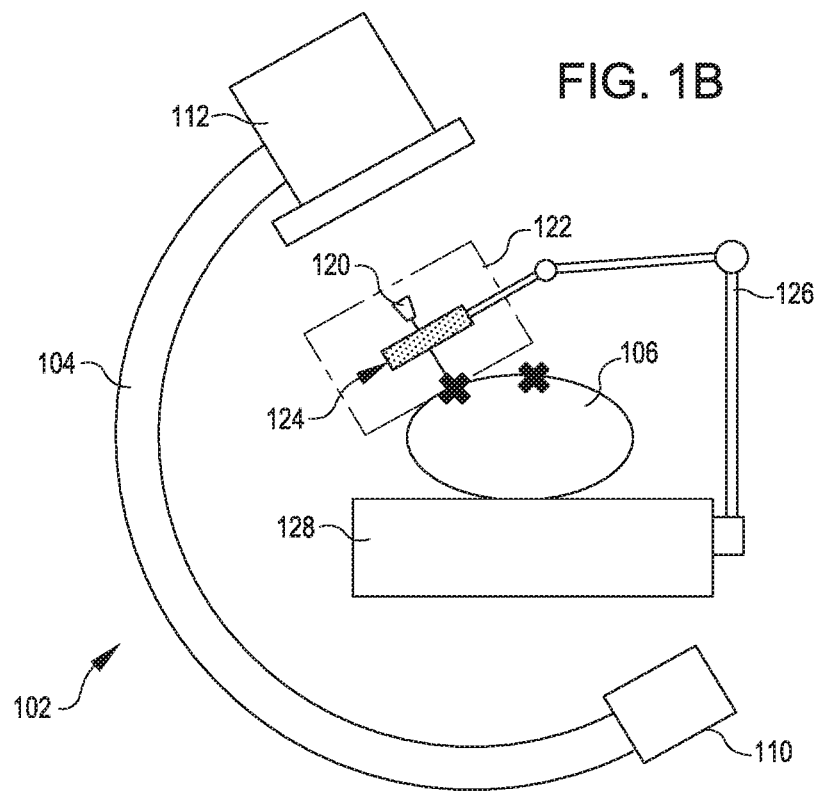
FIG. 1(b) is a schematic drawing of the system when viewed from arrow A in the example embodiment.

FIG. 1(b) is a schematic drawing of the system 102 when viewed from arrow A in the example embodiment. The C-arm 104 comprises an imaging device. The imaging device may be a radioactive imaging device such as, but not limited to, an x-ray imaging device. In alternative example embodiments, any other imaging devices or any other forms of imaging, such as, but not limited to, Magnetic Resonance Imaging (MRI), Computed Tomography (CT)-scans etc., may be used. In the example embodiment, the imaging device comprises an x-ray transmitter 110 and an x-ray receiver 112. The transmission surface or plane of the transmitter 110 is substantially parallel to the receiving surface or plane of the receiver 112.

In the system 102, there is further provided a guidance module 122 for guiding an instrument e.g. a hollow needle 120. The guidance module 122 comprises an apparatus 124 for guiding the instrument and preferably, a support arm 126. The support arm 126 is attachably coupled to the apparatus 124 for placement and support of the apparatus 124 e.g. during a PAK procedure.

In the example embodiment, the apparatus 124 may be attached to the support arm 126, e.g an articulated arm, for quick setup and removal. The support arm 126 takes reference in positioning from a bed/table 128 that the support arm 126 attaches to. This may further reduce the overall time for e.g. a PAK procedure, in addition to the time savings for a procedure provided by the use of the alignment module 108 and/or the apparatus 124.

In the example embodiment, the apparatus 124 can provide a fine adjustment mechanism e.g. for use in a PAK procedure and can provide a desired correction for needle deflections. In the example embodiment, the adjustment may be less than about 2 mm.

In the example embodiment, the apparatus 124 is preferably, either entirely or partially, constructed of material such that shadowing effects during the imaging is substantially reduced and/or prevented. For example, for radioactive imaging such as x-ray imaging, the apparatus 124 is preferably constructed of radio transparent, or radiolucent, or radio translucent, material. Such material may include, but is not limited to, titanium, glass, polystyrene, polyurethane, PVC, polyether ether ketone (PEEK), paper etc.

Furthermore, in the example embodiment, the apparatus 124 further comprises a releasing mechanism (not shown) that may detach the instrument, e.g. the needle 120, from the guidance module 122. The releasing mechanism may facilitate removal of the guidance module 122 from the subject 106 e.g. so that the guidance module 122 is not obstructive to subsequent procedural steps.

Figure 2:
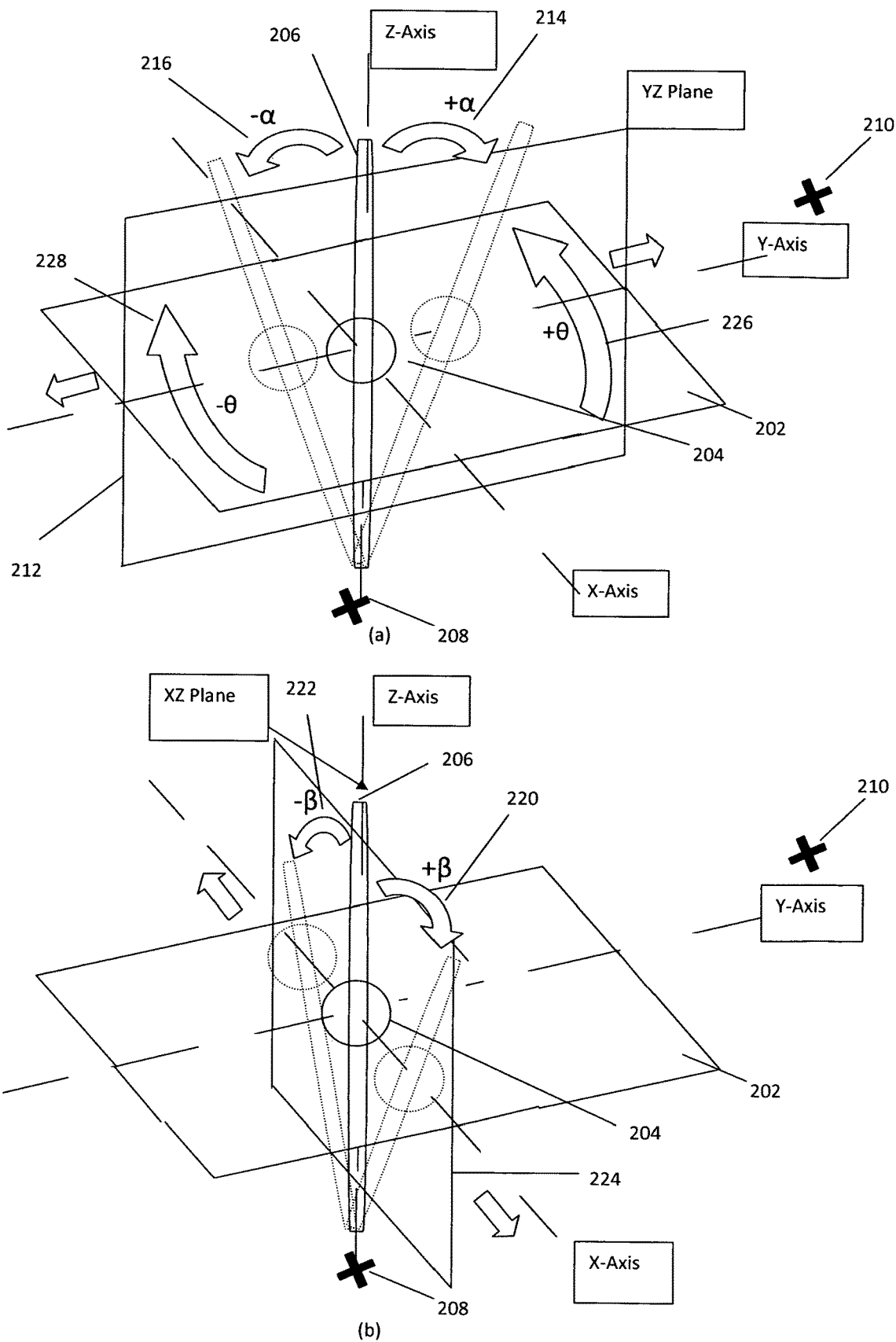
FIGS. 2(a) and (b) are schematic drawings for broadly illustrating an apparatus for guiding an instrument in an example embodiment.

FIGS. 2 (a) and (b) are schematic drawings for broadly illustrating an apparatus for guiding an instrument in an example embodiment. In the example embodiment, the apparatus 202 comprises a holding member or an instrument holder 204. The holding member may be offset from the center of the main body of the apparatus or the holding member may be in the center of the main body. In some embodiments, the instrument holder 204 may further comprise a clamp or plug-shaft assembly for co-operating with a compliance device. In other embodiments, the instrument holder 204 may be an aperture provided on the apparatus 202 to retain/hold an instrument 206.

The apparatus 202 further comprises one or more actuating mechanisms or members or devices for providing translational movement along one or more axis within a plane horizontal with respect to the main body of the apparatus 202 (e.g. the y-axis and/or the x-axis). The translational movement in the above-mentioned plane may cause/impart a movement for an instrument, or rotational movement of the instrument, about a pivot point 208, the pivot point being at the tip of the instrument e.g. when in contact with a subject. The movement of the instrument may be in dual-planes (e.g. in YZ-plane 212 and/or in XZ plane 224). The pivot point 208 is thus external the apparatus 202.

For example, with a translational movement of the instrument holder 204 in the y-axis direction, the instrument 206 may be caused to rotate about the external pivot point 208 in the YZ-plane 212 with angle alpha $\alpha$ (compare numerals 214, 216). With a translational movement of the instrument holder 204 in the x-axis direction, the instrument 206 may be caused to rotate about the external pivot point 208 in the XZ-plane 224 with angle beta $\beta$ (compare numerals 220, 222).

For the axis movement, preferably, a locking member (not shown) may be provided to restrict movement of the holding member (e.g. along the x-direction) such that only further movement of the holding member along a single axis (e.g. along the y-direction) is allowed.

In the example embodiment, the apparatus 202 may be additionally rotated about an axis vertical with respect to the main body of the apparatus 202 (e.g. the z-axis), and within a plane parallel to the plane horizontal with respect to the main body of the apparatus 202. For example, the apparatus 202 may be rotated in a XY-plane with angle theta $\theta$ (compare numerals 226, 228). A rotational locking member (not shown) may be provided to restrict the rotation.

In the example embodiment, e.g. during a PAK process, the apparatus 202 is brought in position at a second marking, e.g. at pivot point 208, on a subject. The apparatus 202 is rotated about the z-axis to orientate or align with a first marking 210 on the subject. After alignment, rotation about the z-axis may be locked. The instrument 206 may then be inserted into the instrument holder 204 and brought into contact with the subject. The pivot point 208 may then be provided at the tip of the instrument in contact with the subject, e.g. about 3 mm insertion into the subject. Dual-plane movement (e.g. in the XZ and YZ planes) may be caused/imparted/provided by the apparatus 202 to the instrument 206 for guiding the instrument 206 into alignment with a target within the subject. The instrument may then be inserted and adjustment of the instrument may still be carried out via the translational movement.

It will be appreciated that the pivot point 208 is not limited to be at the second marking. Rather, the pivot point 208 may be, for example, any point along a line drawn between the first marking 210 and the second marking 208, and inclusive of the first and second markings themselves.

In an alternative example embodiment, the holding member may be in a second plane parallel to the plane horizontal with respect to the main body of the apparatus, e.g. offset at a fixed distance upwards or downwards from the main body. The actuating mechanisms/members are configured to effect the movement of the holding member as translational movements within the second plane.

Figure 3A:
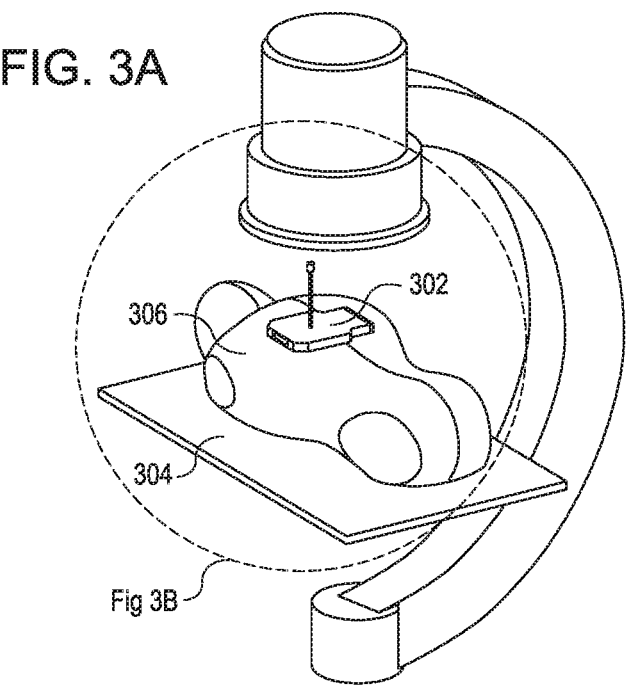
FIG. 3(a) is a schematic drawing illustrating an instrument guidance apparatus in an example embodiment.

FIG. 3(a) is a schematic drawing illustrating an instrument guidance apparatus in an example embodiment. The instrument guidance apparatus 302 is an embodiment of the apparatus 124 of FIG. 1(b). The instrument guidance apparatus 302 is detachably coupled or mounted on a rail (not shown) of a table 304. A subject 306 may be placed on the table/bed 304 and the instrument guidance apparatus 302 is positioned on top of, or over, the subject 306.

Figure 3B:
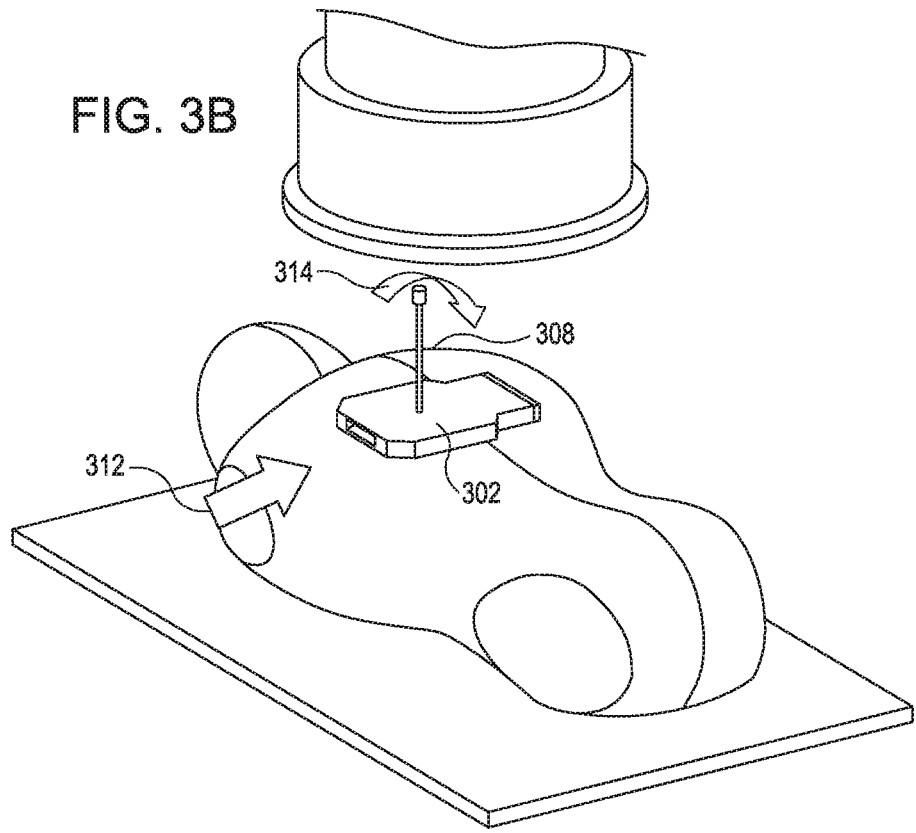
FIG. 3(b) is a zoomed-in view of FIG. 3(a).

FIG. 3(b) is a zoomed-in view of FIG. 3(a). An instrument 308 is shown held/retained by the instrument guidance apparatus 302. The instrument 308 contacts an insertion surface of the subject 306. The tip of the instrument 308 or the point of contact (not shown) is the pivot point (compare 208 of FIGS. 2(a) and (b)) of the instrument 308. Therefore, the pivot point is external to the instrument guidance apparatus 302. An actuating mechanism (not shown) is provided for the instrument guidance apparatus 302 to cause/impart a tilting of the instrument 308 or rotational movement of the instrument 308 about the external pivot point (compare numerals 214, 216 of FIGS. 2(a) and (b)). For example, the actuating mechanism 310 is configured to move along a Y-axis 312 as shown. In this case, a conventional Z-axis is an axis (not shown) perpendicular to the subject 306. The movement along the Y-axis causes the instrument 308 to pivot about the pivot point and in the YZ plane. Compare arrow 314. In the example embodiment, a second actuating mechanism (not shown) may also be provided for X-axis movement.

Preferably, the instrument guidance apparatus 302 is also configured to be rotatable around the Z-axis (compare numerals 226, 228 of FIGS. 2(a) and (b)), i.e. the axis perpendicular to the Y-axis and perpendicular to the subject 206.

In another example embodiment, by additionally providing translational movement in another axis (e.g. X-axis) perpendicular to the axis of movement (e.g. Y-axis), for example, using the second actuating mechanism 316, the needle guidance apparatus may impart/cause rotational movement of the instrument in a XZ-plane (compare 224 of FIGS. 2(a) and (b)) about the pivot point (compare 208 of FIGS. 2(a) and (b)) maintained at the needle tip.

In the example embodiment, the X-axis (and/or Y-axis) translational movement may be provided with "fine" and "coarse" adjustment. Coarse adjustment may be large scale movement e.g. sliding by pulling and pushing an actuating mechanism. Fine adjustment may be provided through rotating fine screw threads e.g. less than about 2 mm screw pitch. The needle guidance apparatus may be provided with a locking member/device that locks actuating for coarse (or large-scale) movement, e.g. during needle insertion, but still allows for fine (or micro-scale) adjustment. During the adjustment, the pivot point is maintained at the tip of the needle so that a more precise trajectory can be achieved during insertion. Preferably, the needle guidance apparatus is configured to be compliant to the tilt of the needle during e.g. XZ-plane movement. For example, a compliance mechanism may be provided. The compliance may be advantageous during insertion when the needle encounters resistance provided by the subject's body. The needle guidance apparatus is also configured to have a release mechanism for detaching the needle from the needle guidance apparatus. For example, the release may be achieved in two or less steps.

Figure 4:
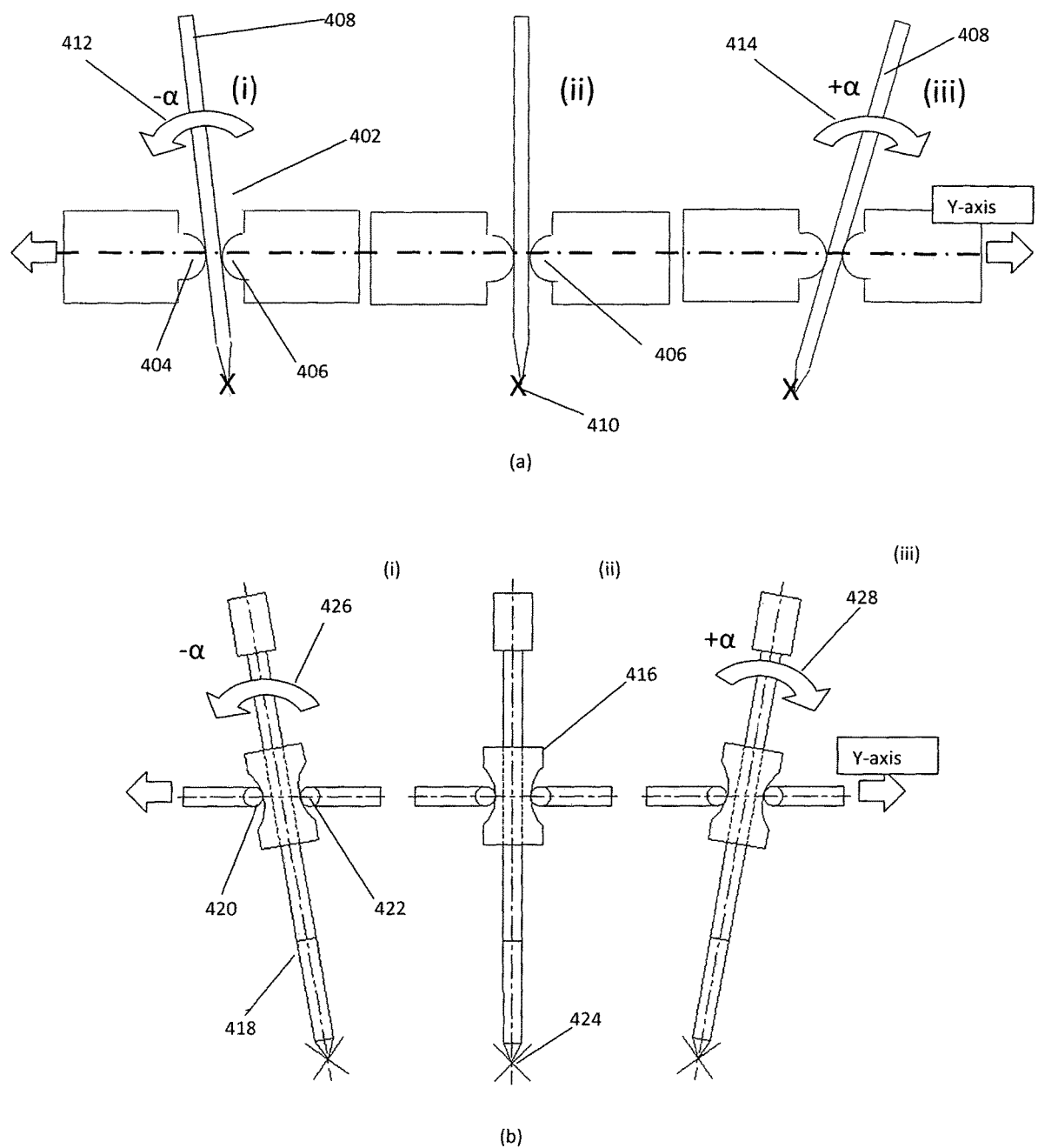
FIGS. 4(a), (b) and (c) are schematic drawings for illustrating different compliance mechanisms in different example embodiments.
Figure 4:
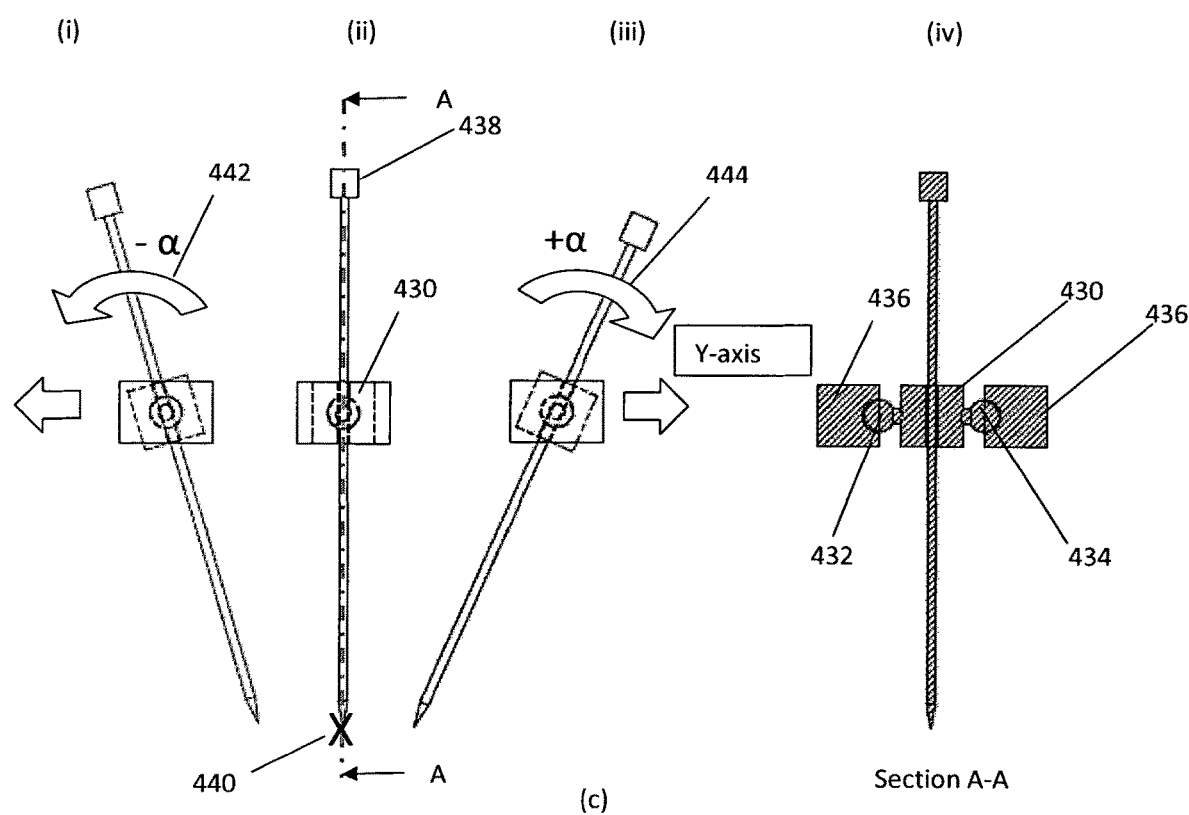

FIGS. 4(a), (b) and (c) are schematic drawings for illustrating different compliance mechanisms in different example embodiments.

In one example embodiment, FIGS. 4(a)(i) to (iii) shows a hole/aperture 402 flanked by semi-ball shaped walls e.g. 404, 406. The aperture 402 functions as a holding member or an instrument holder (compare 204 of FIGS. 2(a) and (b)). A needle 408 may be inserted into the hole/aperture 402. In a neutral position, as shown in FIG. 4(a)(ii), the needle 408 has an external pivot 410 at a contact point e.g. at a surface of a subject. In the example embodiment, for a translational movement of the holding member in a direction along an axis (e.g. a y-axis), a rotational movement of the needle 408 about the pivot point is imparted/caused. As shown exemplarily in FIG. 4(a)(i), in a negative y-axis direction movement, the needle 408 is caused to rotate in a negative angle alpha 412 about the pivot point 410 with the semi-ball shaped walls e.g. 404, 406. As shown exemplarily in FIG. 4(a)(iii), in a positive y-axis direction movement, the needle 408 is caused to rotate in a positive angle alpha 414 about the pivot point 410 with the semi-ball shaped walls e.g. 404, 406. The compliance mechanism described with reference to FIGS. 4(a)(i) to 4(a)(iii) is substantially similar to the compliance mechanism described later with reference to FIGS. 17, 18, 19(a) to (b), 20(a) to (b), 22 and 24(a) to (b).

In one example embodiment, FIGS. 4(b)(i) to (iii) shows a compliance device 416. The compliance device 416 comprises a hollow shaft to receive a needle 418. The compliance device 416 is flanked by semi-ball shaped walls e.g. 420, 422. In a neutral position, as shown in FIG. 4(b)(ii), the needle 418 has an external pivot 424 at a contact point e.g. at a surface of a subject. In the example embodiment, for a translational movement of the holding member in a direction along an axis (e.g. a y-axis), a rotational movement of the needle 418 about the pivot point is imparted/caused. As shown exemplarily in FIG. 4(b)(i), in a negative y-axis direction movement, the needle 418 is caused to rotate in a negative angle alpha 426 about the pivot point 424 with the semi-ball shaped walls e.g. 420, 422. As shown exemplarily in FIG. 4(b)(iii), in a positive y-axis direction movement, the needle 418 is caused to rotate in a positive angle alpha 428 about the pivot point 424 with the semi-ball shaped walls e.g. 420, 422. The compliance mechanism described with reference to FIGS. 4(b)(i) to 4(b)(iii) is substantially similar to the compliance mechanism described later with reference to FIGS. 16, 17 and 18 (a) to (d).

In one example embodiment, FIGS. 4(c)(i) to (iv) shows a compliance device 430. FIG. 4(c)(iv) shows a cross-sectional view of the line A-A of FIG. 4(c)(ii). The compliance device 430 comprises ball-shape rotational joints e.g. 432, 434 for engagement with corresponding sockets/holders provided on a holding member 436. The compliance device 430 also comprises a shaft to receive a needle 438. In a neutral position, as shown in FIG. 4(c)(ii), the needle 438 has an external pivot 440 at a contact point e.g. at a surface of a subject. In the example embodiment, for a translational movement of the holding member in a direction along an axis (e.g. a y-axis), a rotational movement of the needle 438 about the pivot point is imparted/caused. As shown exemplarily in FIG. 4(c)(i), in a negative y-axis direction movement, the needle 438 is caused to rotate in a negative angle alpha 442 about the pivot point 440 with the ball-shape rotational joints e.g. 432, 434 interacting with the corresponding sockets/holders provided on the holding member 436. As shown exemplarily in FIG. 4(c)(iii), in a positive y-axis direction movement, the needle 438 is caused to rotate in a positive angle alpha 444 about the pivot point 440 with the ball-shape rotational joints e.g. 432, 434 interacting with the corresponding sockets/holders provided on the holding member 436. The compliance mechanism described with reference to FIGS. 4(c)(i) to 4(c)(iv) is substantially similar to the compliance mechanism described later with reference to FIGS. 12(a) to (b), 13(a) to (g), 14 and 15 (a) to (d).

Figure 5:
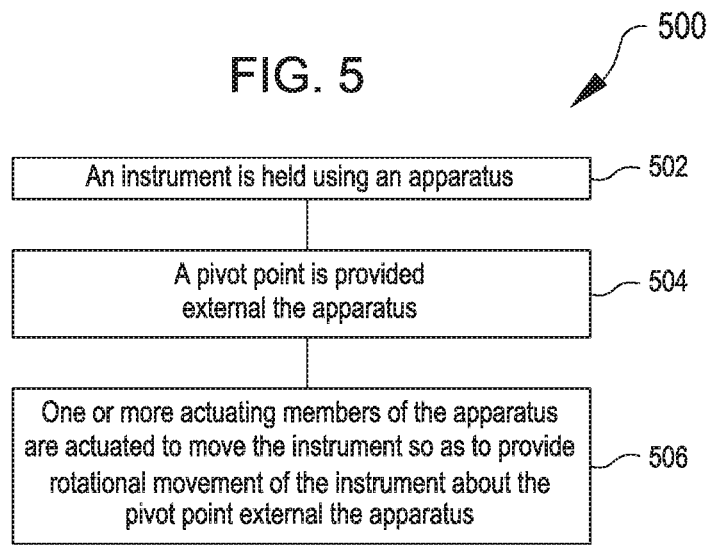
FIG. 5 is a schematic flowchart for illustrating a method for guiding an instrument in an example embodiment.

FIG. 5 is a schematic flowchart 500 for illustrating a method for guiding an instrument in an example embodiment. At step 502, an instrument is held using an apparatus. At step 504, a pivot point is provided external the apparatus. At step 506, one or more actuating members of the apparatus are actuated to move the instrument so as to provide rotational movement of the instrument about the pivot point external the apparatus.

Preferably, during the rotational movement of the instrument about the pivot point external the apparatus, a compliance device (e.g. as described with reference to FIGS. 4(a) to (c)) may be used therein for smoother pivoting motion provided to the instrument.

The method may further comprise, for the step of actuating one or more actuating members to move the instrument, effecting the movement of the instrument in a translational manner within a plane that is parallel to a plane horizontal with respect to a main body of the apparatus.

In the example embodiment, preferably the pivot point is within a subject or a tissue of the subject.

In the example embodiment, the method may further comprise inserting the instrument into a subject, aligning to a target within a subject and using the one or more actuating members of the apparatus.

The method may be used in a PAK procedure.

In another example embodiment, the inventors have recognised that the system 102 may be further enhanced for better accuracy by adding a visual alignment module.

Figure 6:
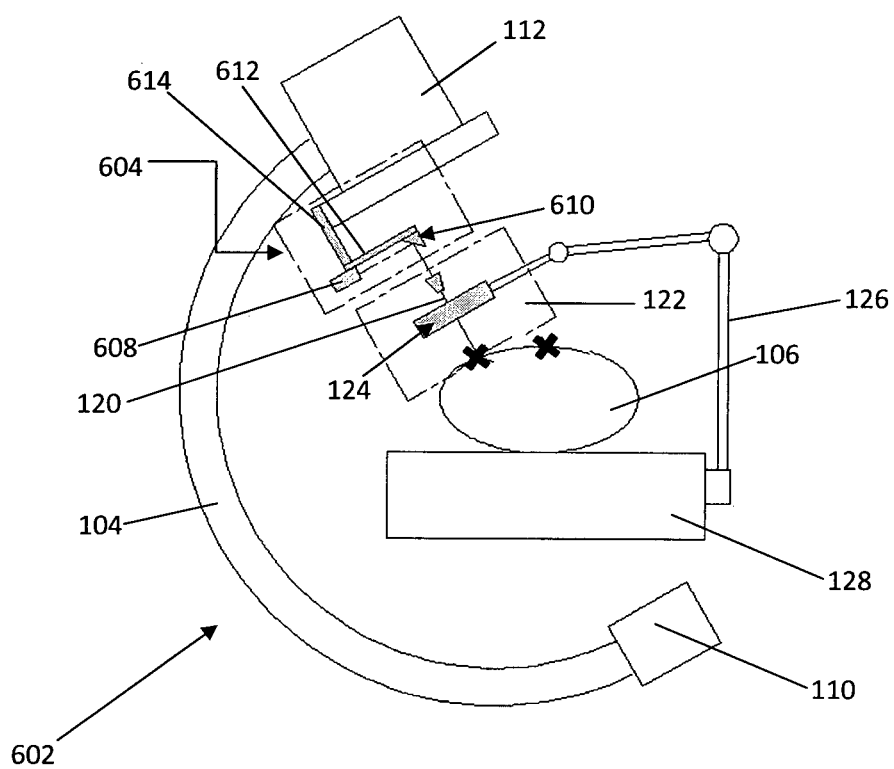
FIG. 6 is a schematic drawing for illustrating exemplary instrument guidance using a visual alignment module in an example embodiment.

FIG. 6 is schematic drawing for illustrating exemplary instrument guidance using a visual alignment module in an example embodiment. Like components function substantially similar to the components described with reference to FIG. 1(b). For the ease of illustration, like numerals are used for description of the like components.

In the system 602, an alignment module 604 is provided and comprises a visible light source 608 and a refraction/reflection member 610. The light source 608 may be, but is not limited to, a laser pointer/source. The refraction/reflection member 610 may be, but is not limited to, a prism. A holding spine 612 is provided to retain and position the prism 610. In the example embodiment, a visible reference on the subject 106 is substantially perpendicular to the transmission surface or plane of the transmitter 110. This may be adjusted by the positioning of the prism 610. Therefore, the visible reference can advantageously provide a perpendicular reference to the x-ray plane.

In the example embodiment, the light source 608 is disposed offset from the transmission path of the x-ray transmitter 110. The prism 610 is disposed in the transmission/imaging path of the x-ray transmitter 110. It has been recognised that the prism 610 is substantially transparent for radioactive imaging. The holding spine 612 is preferably made of material transparent to radioactive imaging, and as the prism 610 is substantially transparent in the transmission/imaging path of the x-ray transmitter 110, the disposal of the light source 608 offset from the transmission/imaging path of the x-ray transmitter 110 can thus advantageously be such that the x-ray image obtained at the receiver 112 is substantially free of shadows.

In the example embodiment, the visible alignment module 604 can enhance insertion accuracy. A micro-mechanism or movable holder 614 may be provided coupled to the laser pointer 608. The movable holder 614 can be used to provide a plane movement along the receiver 112 so that the visible light reference can be projected e.g. onto the subject 106. The visible light reference remains perpendicular to the receiver imaging plane after the adjustment. In the example embodiment, there are provided two movements in the adjustment. While the distance between the laser pointer 608 and the prism 610 is preferably fixed, both components 608, 610 may be rotated along the center axis of the C-arm receiver 112 and their distance from the center is adjustable. That is, the mechanism or movable holder 614 is designed to place the prism 610 (radially and/or rotationally) on any point on the receiver plane using the polar coordinate system. Thus, the visible light source is adjustable within a plane parallel to a plane of the imaging surface.

Figure 7:
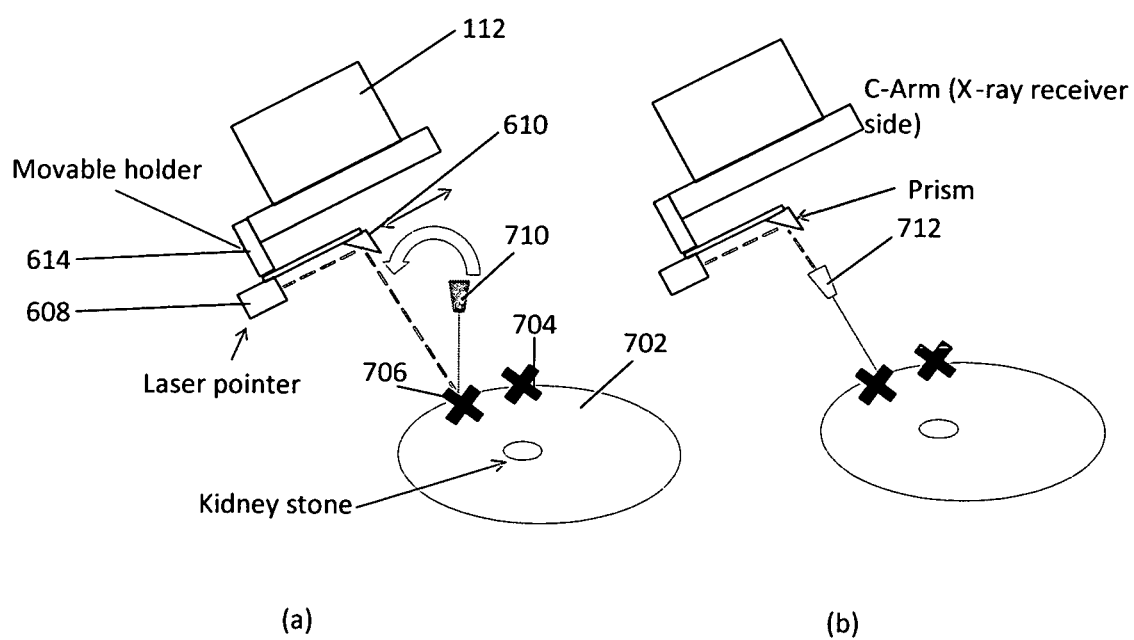
FIGS. 7(a) and (b) are schematic drawings for illustrating use of the visual alignment module of FIG. 6 in an example embodiment.

FIGS. 7(a) and (b) are schematic drawings for illustrating use of the visual alignment module of FIG. 6 in an example embodiment. In FIG. 7(a), a laser beam is projected using the prism 610 at a second marking 706 on a subject 702. The C-arm imaging device is tilted, e.g. to a first marking 704, to obtain images for determination of the target information e.g. depth. The laser beam is thus projected to the second marking 706 and a needle 710 can be guided to a position for accessing the target. The needle 710 contacts the subject 702 at the laser beam. Guidance of the needle 710 is based on dual-planes (e.g. XZ and YZ planes) movement as described based on FIGS. 2(a) and (b). The guidance can be based on images of the needle 710. For example, if the needle 710 is aligned with the laser beam and thus, the transmission/imaging path of the x-ray imaging, the image may show the end of the needle without showing the stem of the needle.

In FIG. 7(b), the laser beam is projected to the end 712 of the needle 710. Insertion accuracy is advantageously improved by aligning the target, the tip and the hub/end of the needle in line with the plane of the x-ray imaging.

Figure 8:
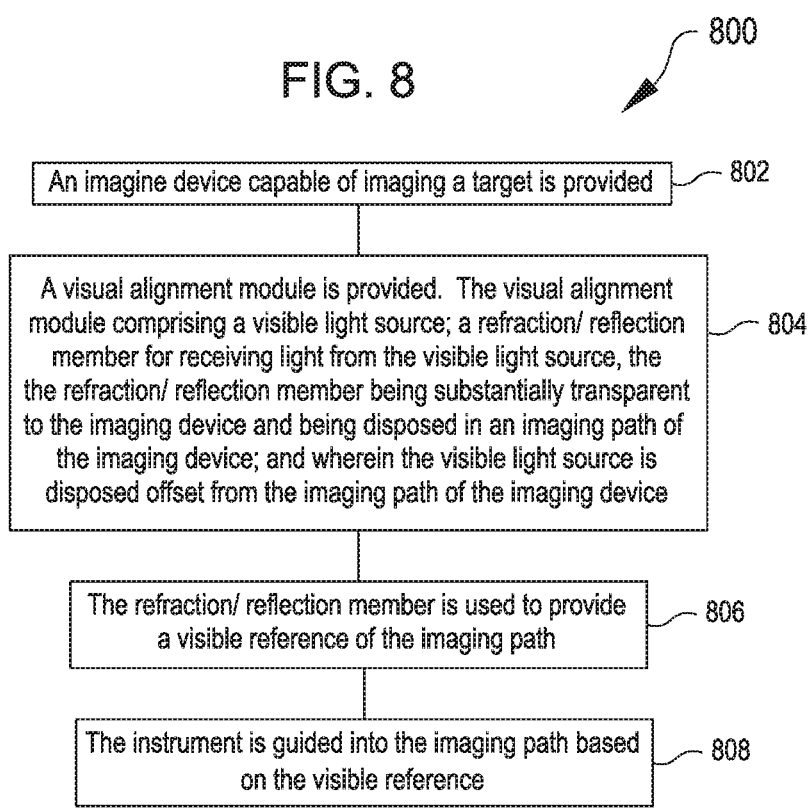
FIG. 8 is a schematic flowchart for illustrating a method for providing a visible reference to guide an instrument in an example embodiment.

FIG. 8 is a schematic flowchart 800 for illustrating a method for providing a visible reference to guide an instrument in an example embodiment. At step 802, an imaging device capable of imaging a target is provided. At step 804, a visual alignment module is provided. The visual alignment module comprising a visible light source; a refraction/reflection member for receiving light from the visible light source, the refraction/reflection member being substantially transparent to the imaging device and being disposed in an imaging path of the imaging device; and wherein the visible light source is disposed offset from the imaging path of the imaging device. At step 806, the refraction/reflection member is used to provide a visible reference of the imaging path. At step 808, the instrument is guided into the imaging path based on the visible reference.

Figure 9:
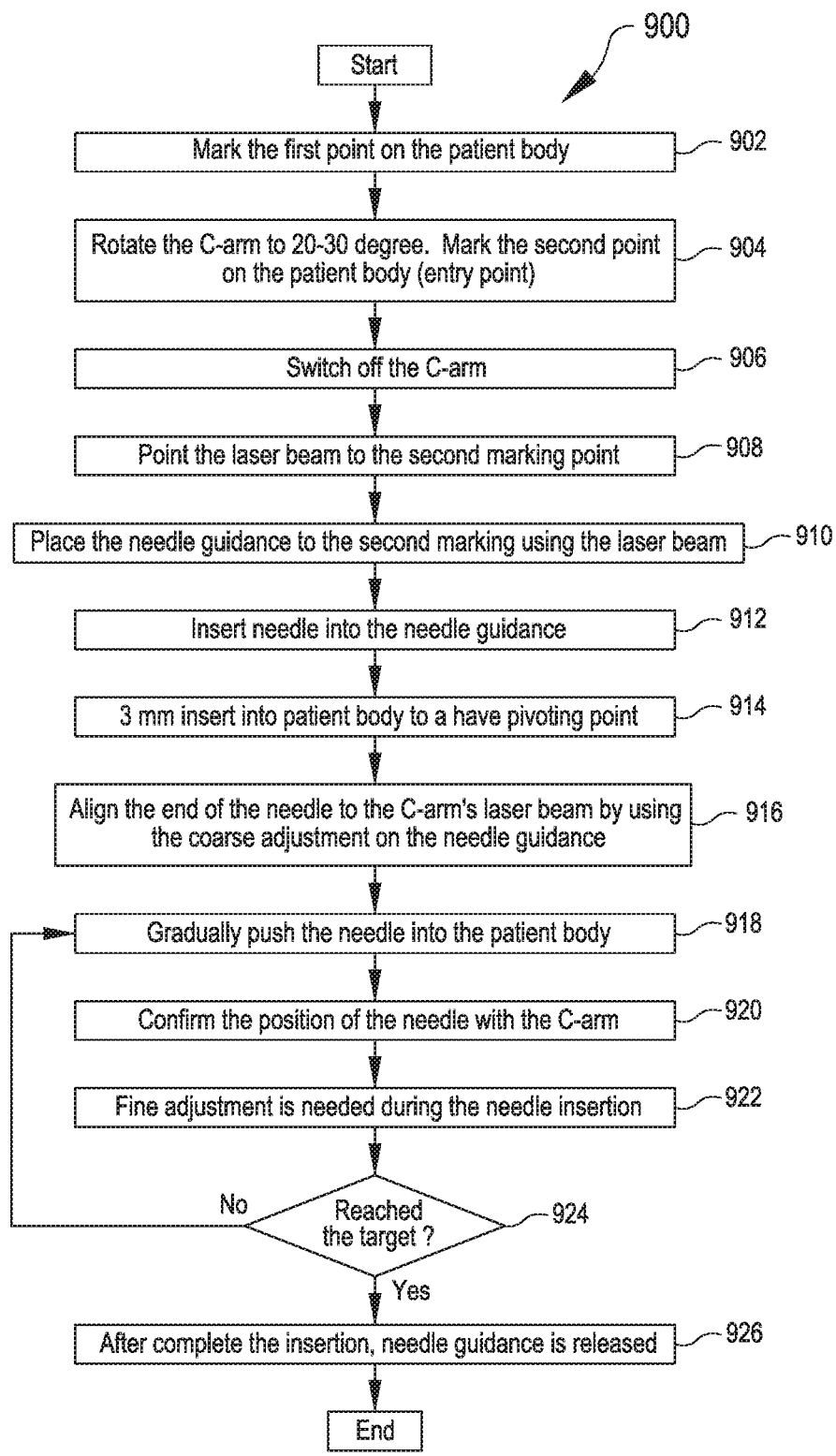
FIG. 9 is a schematic flowchart for illustrating a process flow for accessing a target in an example embodiment.

FIG. 9 is a schematic flowchart 900 for illustrating a process flow for accessing a target in an example embodiment. A system and apparatus for guiding an instrument is used. In the example embodiment, the instrument is a hollow needle. The imaging used is x-ray imaging. The system and apparatus are substantially similar to the system 602 described with reference to FIGS. 6, 7(a) and 7(b), and the apparatus described with reference to FIGS. 2(a) and 2(b). For the alignment module, a laser pointer and prism are used.

At step 902, a first marking is marked on a subject's body. This may be a marker, pen or pencil marking etc. for reference. One or more x-ray images are taken at this start position.

At step 904, the C-arm is rotated for taking additional one or more x-ray images. The rotation of the C-arm may be about 20-30 degrees from the start position. From the images obtained, target information, e.g. depth, is determined. A second marking is marked on the subject's body to designate an entry point for the needle.

At step 906, the x-ray imaging device is switched off for the guidance of the needle. It has been recognized by the inventors that the switching off the x-ray imaging device at this stage can shorten the exposure of the user etc. to the radioactive imaging that may be harmful to health.

At step 908, the laser pointer is switched on and the laser beam is projected to the second marking.

At step 910, the needle guidance apparatus is positioned at the second marking. At step 912, the needle is inserted into the guidance apparatus which holds/retains the needle.

At step 914, the needle is inserted by about 3 mm into the subject's body to obtain a pivot point for the needle. It will be appreciated that the pivot point may also be obtained without insertion, e.g. upon surface contact with the subject body. The x-ray imaging device is then switched on.

At step 916, the needle is guided in e.g. XZ and YZ planes movement using the guidance apparatus, to be aligned to the laser beam. The alignment is confirmed from one or more x-ray images taken at this step. Coarse or relatively large scale movement may be used for the alignment.

At step 918, the needle is inserted incrementally into the subject. At step 920, the position of the needle can be determined using the x-ray imaging. This may comprise rotation of the C-arm.

At step 922, adjustment of the needle, e.g. fine adjustment of the needle may be performed for the insertion of the needle. This may be performed due to minute deviation of the needle due to resistance by the subject's body.

At step 924, x-ray imaging is used to determine whether the needle has accessed the target. Preferably, the user may also use tactile feedback on the needle to determine whether the needle has accessed the target. If the target has not been accessed, the process loops to step 918.

At step 926, after the target is accessed, the insertion is completed. The needle guidance apparatus or the needle is released.

Figure 10:
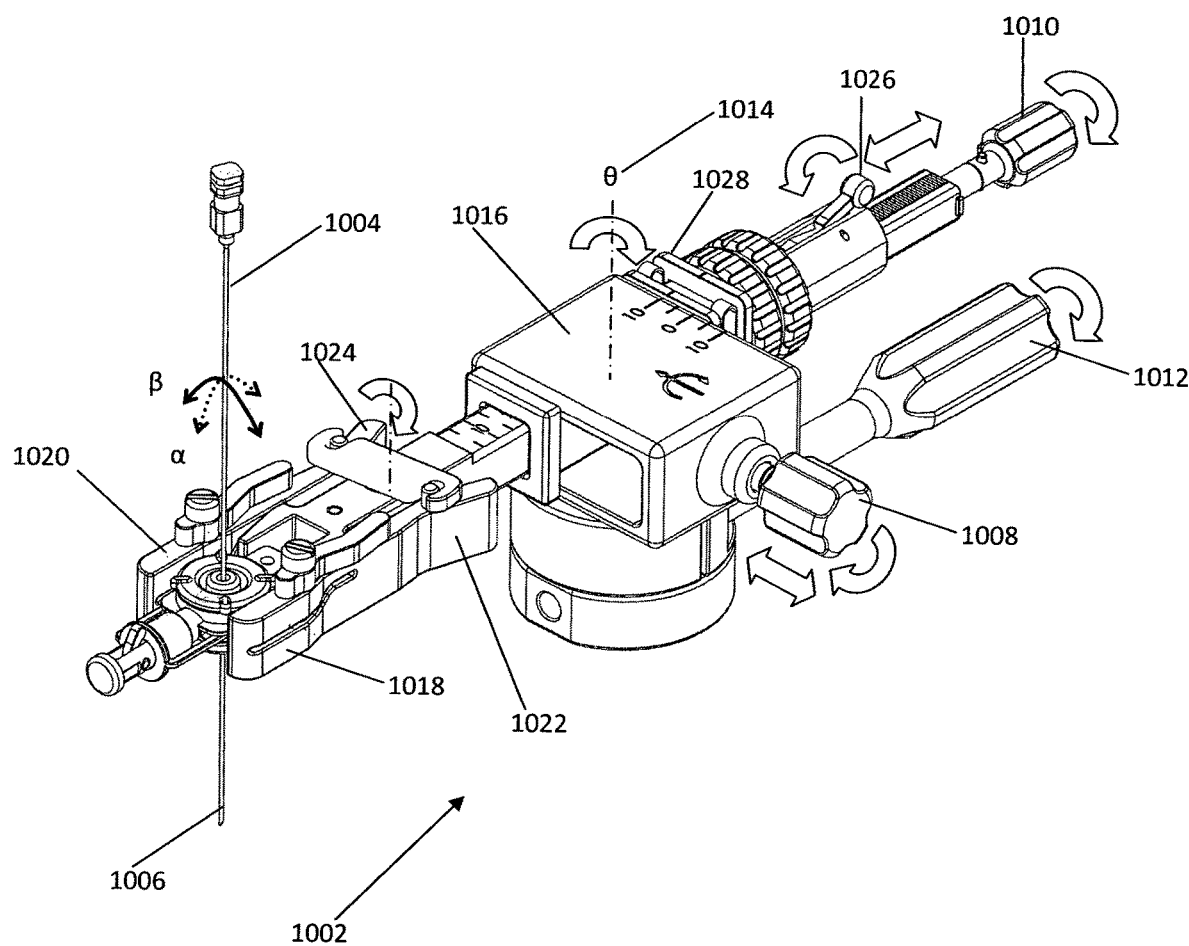
FIG. 10 is a schematic perspective view drawing of an apparatus for guiding an instrument in an example embodiment.

FIG. 10 is a schematic perspective view drawing of an apparatus for guiding an instrument in an example embodiment. The apparatus 1002 can provide e.g. XZ and YZ planes movement for an instrument such as a hollow needle 1004. Compare rotation/tilting angle beta β for x-axis movement about a pivot point 1006 at the tip of the needle 1004, and rotation/tilting angle alpha α for y-axis movement about the pivot point 1006 at the tip of the needle 1004. The pivot point is therefore external to the apparatus 1002. A x-rod 1008 is provided as an actuating member/mechanism to actuate the x-axis movement. A y-rod 1010 is provided as a second actuating member/mechanism to actuate the y-axis movement. A handle 1012 is provided as a third actuating member/mechanism to actuate rotation of the apparatus 1002 about a z-axis, i.e. the axis passing vertically through the center of the apparatus 1002. Compare angle θ 1014. That is, the handle 1012 may function as a rotation member for the apparatus 1002. A spring collet and a slit clamp assembly (not shown) connected to the handle 1012 can function as a rotational locking member for restricting rotation of the apparatus 1002.

In the example embodiment, the needle insertion point, e.g. at pivot point 1006, is offset from the main body 1016 of the apparatus 1002. One advantage is that the offset may maximize visibility of a user of the needle insertion point on a subject. Further, the offset may eliminate the likelihood of shadows cast, e.g. of the apparatus 1002, over the target of the subject during radioactive imaging. In this regard, the apparatus 1002 is also preferably, either entirely or partially, constructed of material such that shadowing effects during the imaging is substantially reduced and/or prevented. For example, at least a holding member of the apparatus 1002 may be constructed of such material. For example, for radioactive imaging such as x-ray imaging, the apparatus 124 is preferably constructed of radio transparent, or radio-lucent, or radio translucent, material. Such material may include, but is not limited to, titanium, glass, polystyrene, polyurethane, PVC, polyether ether ketone (PEEK), paper etc.

In the example embodiment, a holding member e.g. in the form of a clamp device/mechanism for holding an instrument is provided. A clamp device/mechanism comprising clamp members/fingers 1018, 1020 can retain/hold the needle 1004. The clamp fingers 1018, 1020 can also allow "quick" and simple release of the needle 1004 from the apparatus 1002, by the user applying pressure to clamp release end portions 1022, 1024 of the clamp fingers 1018, 1020.

In the example embodiment, a cam knob 1026 is provided for locking the y-rod 1010 after coarse or large-scale adjustment while still allowing fine or small-scale adjustment by rotation of the y-rod 1010.

Preferably, in the example embodiment, a locking member is provided in the x-direction to restrict movement in the x-direction such that only further movement along a single axis (y-axis) is allowed.

Thus, the apparatus 1002 can provide the alignment of the needle insertion plane and the imaging plane, e.g. x-ray plane, using the needle 1004 itself. That is, during practical use, the apparatus 1002 may hold the needle 1004 to align parallel, preferably directly above, a line connecting a first marking and a second marking on a subject. In this position, the needle 1004 may be substantially horizontal with respect to a surface of the subject. The needle 1004 may then be drawn progressively by the apparatus 1002 towards an upright or vertical position along the alignment or the connecting line for beginning of the process to access a target within the subject.

Figure 11:
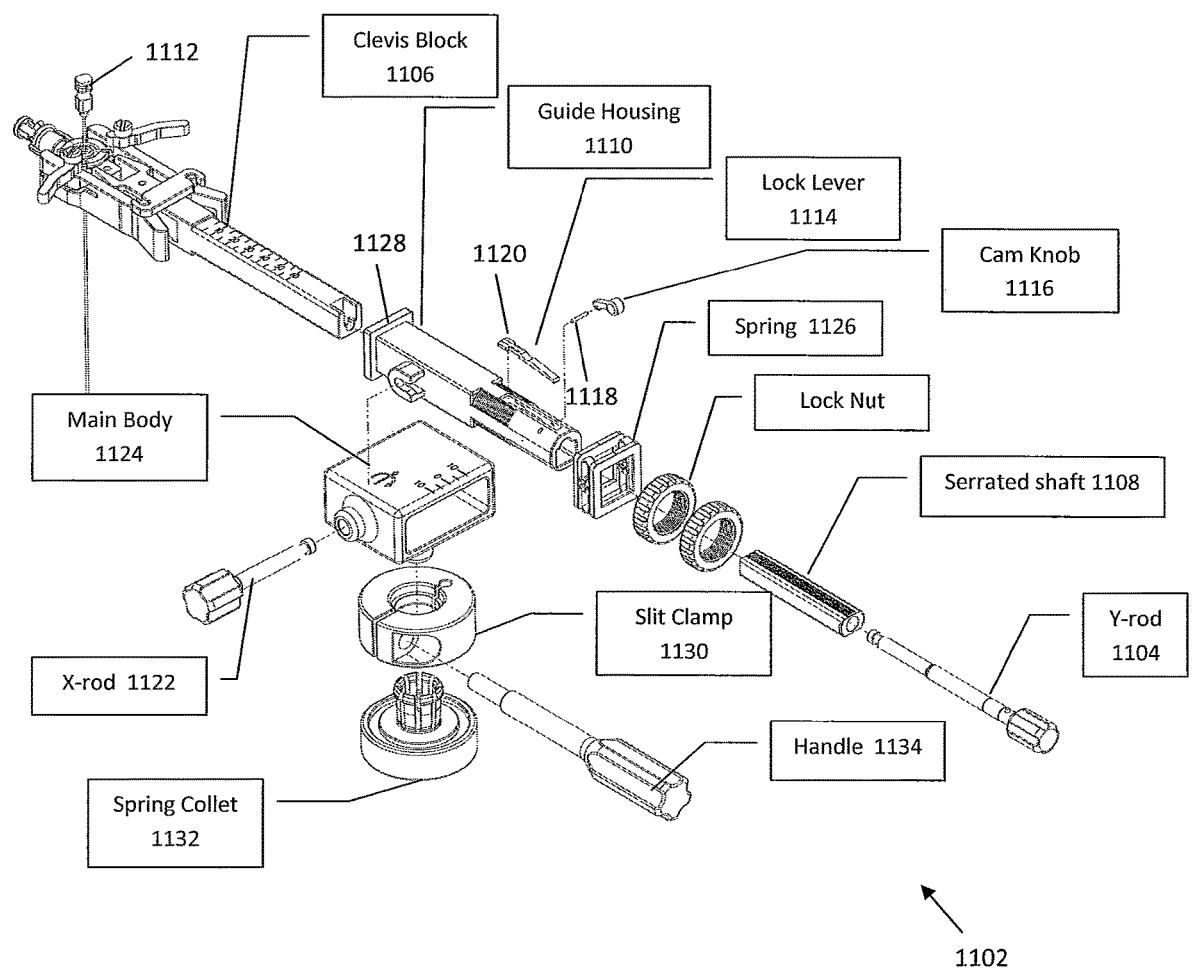
FIG. 11 is an exploded view of an apparatus for guiding an instrument in an example embodiment.

FIG. 11 is an exploded view of an apparatus for guiding an instrument in an example embodiment. The apparatus 1102 is substantially identical to the apparatus 1002 described with reference to FIG. 10.

A y-rod 1104 is provided for coupling to a clevis block 1106 via a serrated shaft 1108. In the example embodiment, the clevis block 1106 is an extendable member that can be coupled to a main body 1124 and the clevis block 1106 is capable of offsetting a position of the clamp fingers (compare 1018, 1020 of FIG. 10) from the main body 1124. The coupling is housed in a guide housing 1110. A y-axis movement can be achieved by applying translational force, e.g. pushing or pulling the y-rod 904, that in turn moves the coupling. It is recognised that such movement can give a coarse or large scale adjustment to an instrument e.g. a hollow needle 1112.

A locking/lock lever 1114 is provided on the guide housing 1110. A cam knob 1116 is provided to engage the lock lever 1114. The cam knob 1116 is rotatable about a cam shaft 1118. By rotating or "flipping" the cam knob in a y-axis direction, the cam knob can engage a jaw portion 1120 of the lock lever 1114 to contact serrations of the serrated shaft 1108. This can lock the coupling in the y-direction. Coarse adjustment is prevented when the lock is engaged. The y-rod 1104 can still further engage the serrated shaft 1108 via fine screw threads (not shown) within the serrated shaft 1108 to enable fine or small scale adjustment in the y-direction for the needle 1112.

A x-rod 1122 is provided for coupling to the guide housing 1110 via fine screw threads (not shown) within the main body 1124 of the apparatus 1102. A resilient member such as a spring device 1126 (compare numeral 1028 of FIG. 10) is provided. The spring device 1126 is slidable along the guide housing 1110 to cause an opposite end of the main body 1124 to abut against an end stopper 1128 of the guide housing 1110. This allows one degree of freedom and can provide guidance in the x-direction. The x-rod 1122 can be rotated either clockwise or counter-clockwise, for forward or reverse direction respectively, to adjust the needle 1112 in the x-direction.

The main body 1124 is disposed or can rest/sit on a slit clamp 1130. The slit clamp 1130 can in turn be mounted to a spring collet 1132. The arrangement can provide the theta θ angle adjustment/rotation (compare 1014 of FIG. 10) for the apparatus 1102. A handle 1134 with a threaded end is provided for locking the apparatus 1102 in position after a desired rotation about angle θ. For locking the rotational movement of the apparatus 1102, the handle 1134 is used to tighten the slit clamp 1130, or to cause the circumference of the slit clamp to be smaller, around the spring collet 1132. As the freedom of movement of the spring collet 1132 is restricted, rotational movement is locked or restricted.

Figure 12:
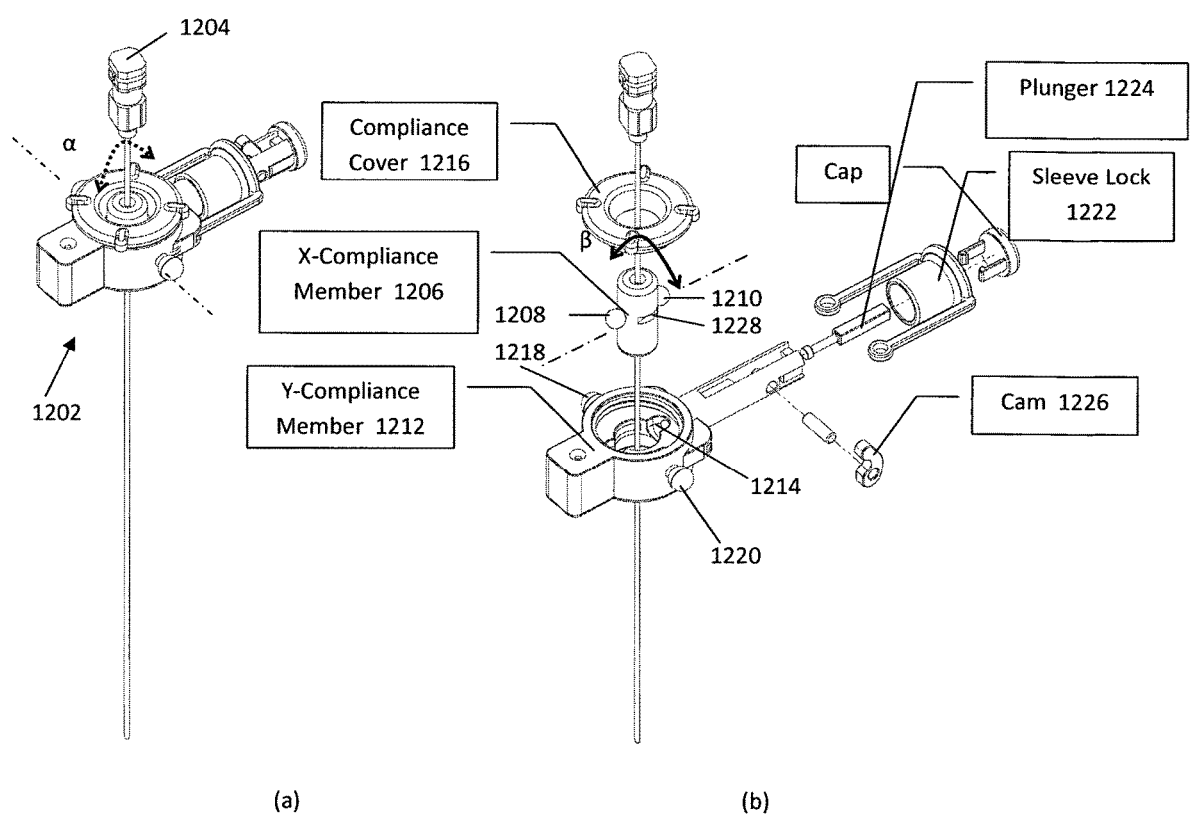
FIG. 12(a) is a schematic drawing for illustrating a compliance device in an example embodiment.
FIG. 12(b) is an exploded view of the compliance device of FIG. 12(a).

FIG. 12(a) is a schematic drawing for illustrating a compliance device in an example embodiment. The compliance device 1202 may be used together, or to co-operate, with the apparatus 1002 or 1102 as described with reference to FIGS. 10 and 11 respectively. The compliance device 1202 can be used to hold/retain an instrument such as a hollow needle 1204. Also shown are rotation/tilting angle beta β for x-axis movement about a pivot point at the tip of the needle 1204, and rotation/tilting angle alpha α for y-axis movement about the pivot point at the tip of the needle 1204.

In some embodiments, the compliance device 1202 is preferably substantially constructed of material such that shadowing effects during the imaging is substantially reduced and/or prevented. For example, for radioactive imaging such as x-ray imaging, the compliance device 1202 is preferably constructed of radio transparent, or radiolucent, or radio translucent, material. Such material may include, but is not limited to, titanium, glass, polystyrene, polyurethane, PVC, polyether ether ketone (PEEK), paper etc.

FIG. 12(b) is an exploded view of the compliance device of FIG. 12(a). The compliance device 1202 comprises a x-compliance member 1206 having with a pair of spherical ball joints 1208, 1210 at opposite sides of the x-compliance member 1206. The compliance device 1202 also comprises a y-compliance member 1212. The ball joints 1208, 1210 can rest on/within corresponding sockets/holders e.g. 1214 provided on the y-compliance member 1212. Thus, the x-compliance member 1206 is capable of pivoting/rotating with respect to the y-compliance member 1212. The x-compliance member 1206 is also provided with grooves e.g. 1228 for locking purposes.

A compliance cover 1216 is provided for retaining the x-compliance member 1206 in position within the y-compliance member 1212 and effectively allows rotation or movement of the needle 1204 in the XZ-plane. In the example embodiment, the y-compliance member 1212 comprises a pair of ball joints 1218, 1220 located opposite each other for engagement with corresponding sockets/holders provided on clamp members/fingers (compare 1018, 1020 of FIG. 10, not shown in FIG. 12(b)) of a clamp device/mechanism. Thus, the y-compliance member 1212 is capable of providing rotation or movement of the needle 1204 in the YZ-plane.

In the example embodiment, the sets of ball joints 1208, 1210, 1218, 1220 are arranged in a perpendicular relationship to provide a compliance of the needle 1204 in a universal direction.

The compliance device 1202 further comprises a sleeve lock 1222, a plunger 1224 and a cam 1226. These components 1222, 1224 and 1226 can work in combination to lock the x-compliance member 1206 in different angular positions.

FIGS. 13(a) to (g) are provided for illustrating maintaining the x-compliance member 1206 (FIG. 12(b)) in different angular positions. For ease of description, like numerals are used to refer to similar components from FIGS. 12(a) and (b).

Figure 13:
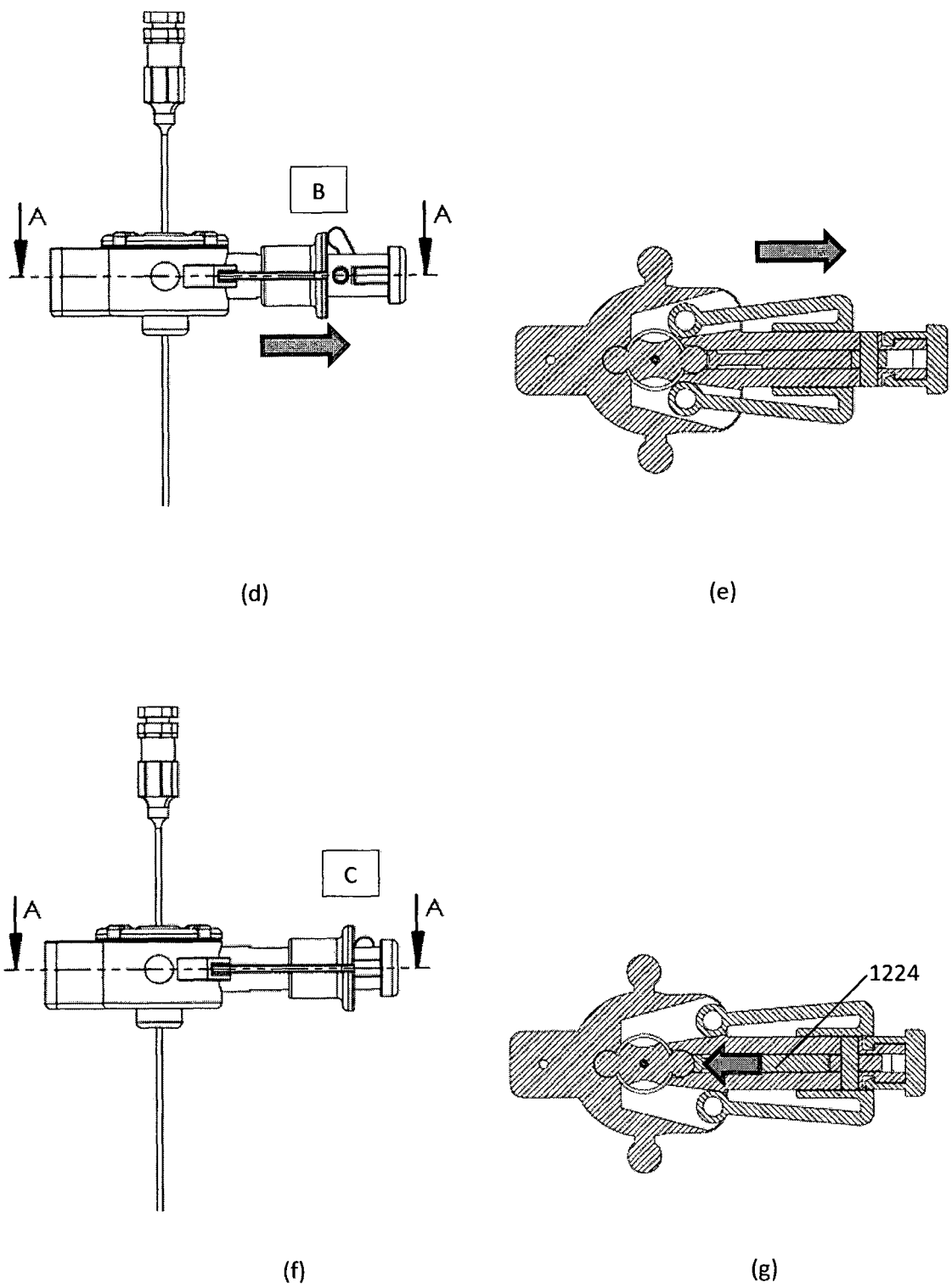
FIGS. 13(a) to (g) are provided for illustrating maintaining a x-compliance member in different angular positions in an example embodiment.

FIG. 13(a) is a schematic cross-sectional drawing of the compliance device 1202 (FIG. 12(a)). The x-compliance member 1206 can be maintained in three different engaging positions (denoted by positions A, B and C) by shifting/moving the sleeve lock 1222 either towards or away (compare numeral 1302) from the x-compliance member 1206. The moving/shifting of the sleeve lock 1222 may be due to an exertion of force or pressure by a user.

FIG. 13(b) is a schematic side view drawing of the compliance device 1202 for illustrating position A. FIG. 13(c) is a schematic cross-sectional top view taken along line AA of the compliance device 1202 in position A. Moving the sleeve lock 1222 towards the x-compliance member 1206 (see position A) causes engagement of ring ends 1304, 1306 of the sleeve lock 1222 with grooves (compare 1228 of FIG. 12(b)) of the x-compliance member 1206. This locks the x-compliance member 1206 in a perpendicular position (i.e. parallel to the z-axis).

FIG. 13(d) is a schematic side view drawing of the compliance device 1202 for illustrating position B. FIG. 13(e) is a schematic cross-sectional top view taken along line AA of the compliance device 1202 in position B. Moving the sleeve lock 1222 to the middle position (i.e. position B) causes disengagement of the ring ends 1304, 1306 of the sleeve lock 1222 with the grooves (compare 1228 of FIG. 12(b)) of the x-compliance member 1206. Thus, the x-compliance member 1206 is allowed to rotate freely.

FIG. 13(f) is a schematic side view drawing of the compliance device 1202 for illustrating position C. FIG. 13(g) is a schematic cross-sectional top view taken along line AA of the compliance device 1202 in position C. Shifting the sleeve lock 1222 further away from the x-compliance member 1206 (i.e. position C) has an effect of activating a plunger assembly, e.g. the cam 1226 and the plunger 1224. With reference to FIG. 13(a), a stop end 1308 engages the cam 1226 that in turn rotates about the cam shaft 1310. The rotation of the cam 1226 causes an engagement of the plunger 1224. In the engagement, the plunger 1224 is moved towards and engages the x-compliance member 1206. A compressive force is thus applied by the plunger 1224 onto the x-compliance member 1206. This in turn locks the x-compliance member 1206 at the last adjusted angular position.

The three engaging positions A, B and C may allow flexibility between serving as rotational compliance about the xz-plane or as a fixed guide.

Thus, for example, during a PAK procedure, a needle shaft e.g. 1312 is inserted through a hole-passage of the x-compliance member 1206. The needle tip is inserted into a top surface (e.g. skin surface) of a subject. With the needle tip functioning as a pivot and the x-compliance member 1206 functioning as a needle guide, there is only a single DOF (degree of freedom) for the needle to be inserted further into the subject until the target is accessed. This advantageously reduces the likelihood of error e.g. during insertion of the needle.

FIG. 14 is an exploded view of a clamping mechanism/device of the apparatus of FIG. 11. The clevis block 1106 is slidable within or extendable from the main body 1124 to provide movement along the y-axis. An attachment end 1402 of the clevis block 1106 is provided for holding clamp members/fingers 1404, 1406 and a compliance device 1408 (compare 1202 of FIG. 12(a)). Thus, the clevis block 1106 facilitates the retention/holding of and manoeuvring/movement of an instrument e.g. needle 1410.

The fingers 1404, 1406 may be held together and secured in position with a pin 1412 that may pass through the clevis block 1106. A resilient member in the form of a leaf spring 1414 is provided to, in turn, provide retention force to hold the compliance device 1408 held by ball joints e.g. 1416 and corresponding sockets e.g. 1418. The leaf spring 1414 provides an abutting/resilient/urging force at ends 1420, 1422 against corresponding slots e.g. 1424 of the fingers 1404, 1406, to urge the fingers 1404, 1406 towards each other.

A safety lock 1426 is provided for securing the fingers 1404, 1406 via locking posts/stems 1428, 1430 to prevent the compliance device 1408 from being unintentionally released from the fingers 1404, 1406 e.g. during needle adjustment and/or insertion process. That is, when the safety lock 1426 is engaged, the compliance device 1408 is held by the fingers 1404, 1406 and is substantially prevented from slackening. Thus, the safety lock 1426 functions as a finger lock member. It will be appreciated that the safety lock 1426 may take other forms such as, but not limited to, the lock 1426 comprising stems instead to engage corresponding slots provided on fingers 1404, 1406, or grooves provided within fingers 1404, 1406 etc. Ball lock levers or locking levers e.g. 1432 are provided for increasing/tightening the grip exerted on the ball joints e.g. 1416 of the compliance device 1408 by the fingers 1404, 1406 to prevent rotation from the last compliance position of the compliance device 1408.

FIGS. 15(a) to (d) are schematic drawings for illustrating engagement and retention/holding of a compliance device in an example embodiment. For ease of description, like numerals are used to refer to similar components from FIG. 14.

Figure 15A:
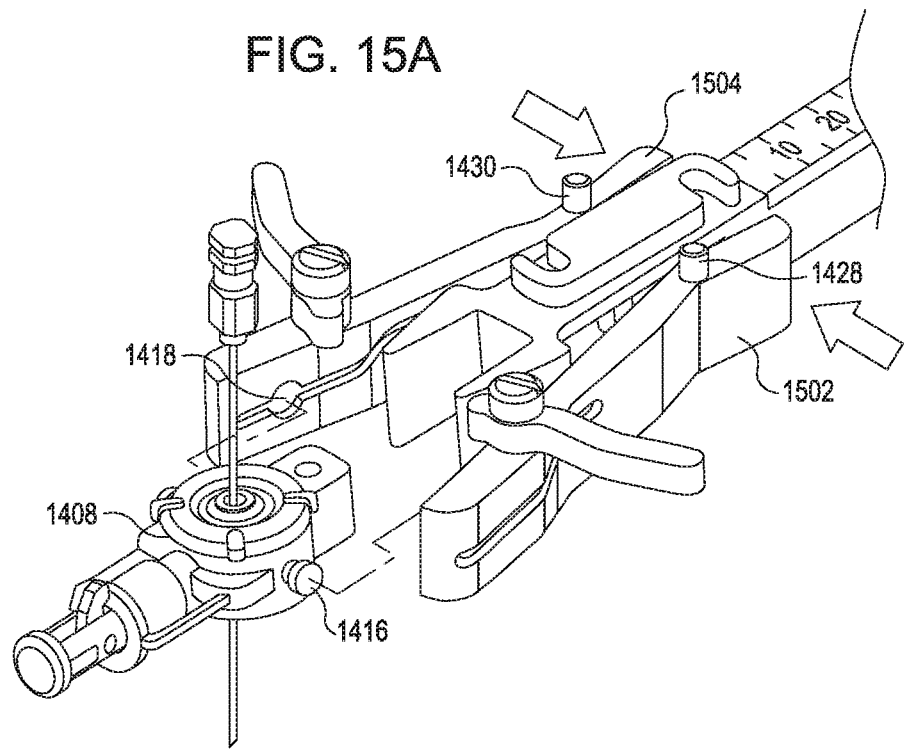
FIGS. 15(a) to (d) are schematic drawings for illustrating engagement and retention/holding of a compliance device in an example embodiment.

With reference to FIG. 15(a), to engage the compliance device 1408, a depressive force is exerted at clamp release end portions 1502, 1504 of the clamp fingers 1404, 1406. Thus, the fingers 1404, 1406 are urged open and allow the compliance device 1408 to be secured/attached onto the inner surfaces of the fingers 1404, 1406 using the ball joints e.g. 1416 and the corresponding socket joints e.g. 1418. The depressive force at the clamp release end portions 1502, 1504 is then removed.

Figure 15B:
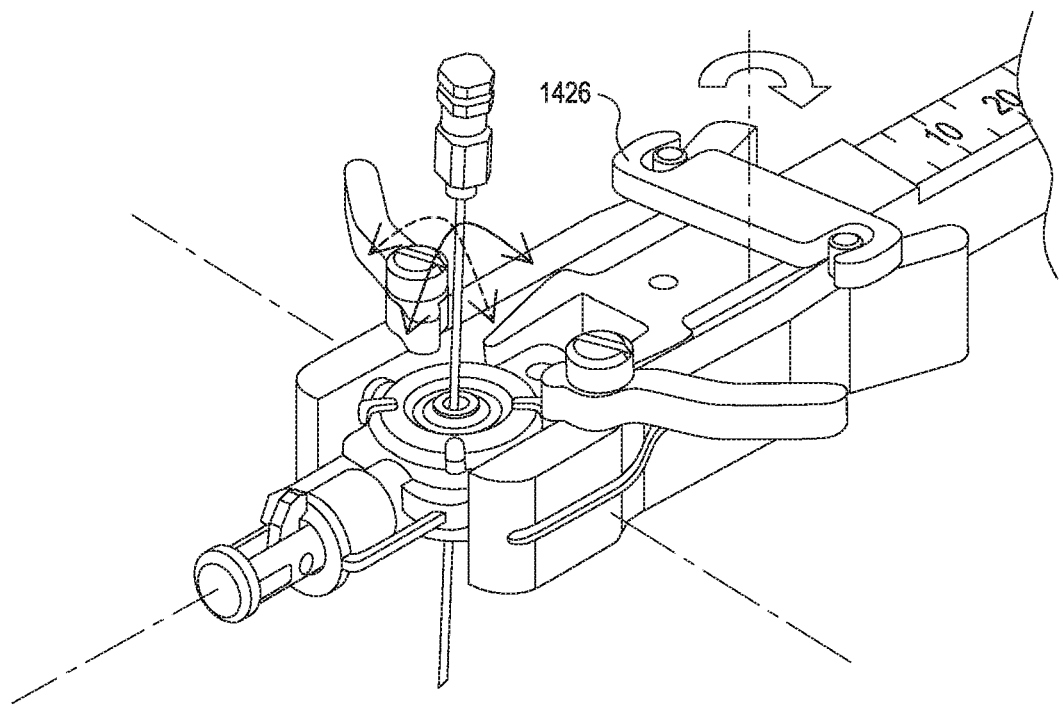

With reference to FIG. 15(b), the safety lock 1426 is rotated to engage the locking posts/stems 1428, 1430. Thus, the safety lock 1426 retains/holds the clamp fingers 1404, 1406 in position to prevent the fingers 1404, 1406 from opening outward e.g. during needle alignment and insertion processes. With the safety lock 1426 engaged, the compliance device 1408 is able to rotate freely only about one axis, the freedom provided by the inner x-compliance member of the compliance device 1408. The rotational motion is shown by the solid arrow line. The locking of movement of the x-compliance member may be achieved by the plunger assembly described with reference to FIG. 13(g).

Figure 15C:
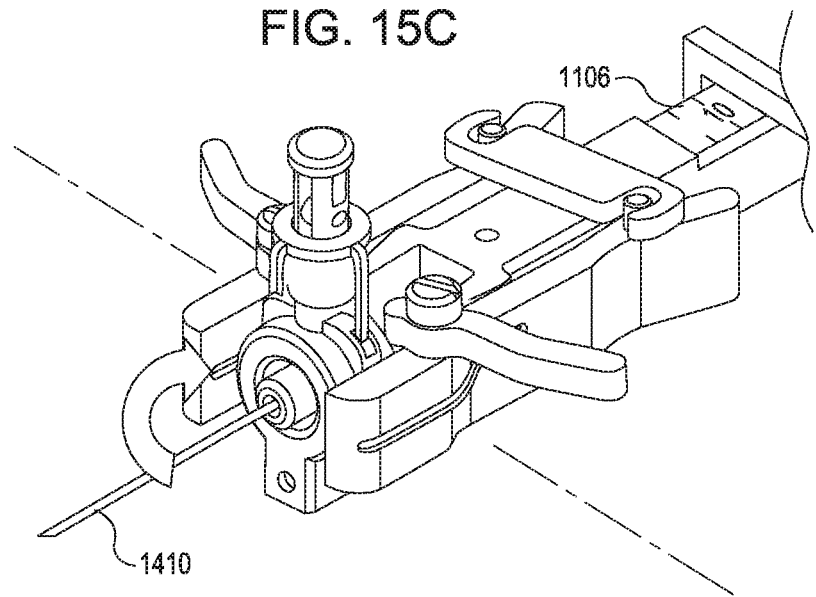

With reference to FIG. 15(c), the compliance device 1408 can be rotated through different angles for alignment and insertion purposes. As shown in FIG. 15(c), the needle 1410 is rotated parallel to the clevis block 1106 (and thus the apparatus) e.g. to align a first marking and a second marking on a surface with an x-ray image captured. The overlapping of the needle image over an image of a target may confirm an insertion path and thus, may facilitate a user decision on an entry point.

Figure 15D:
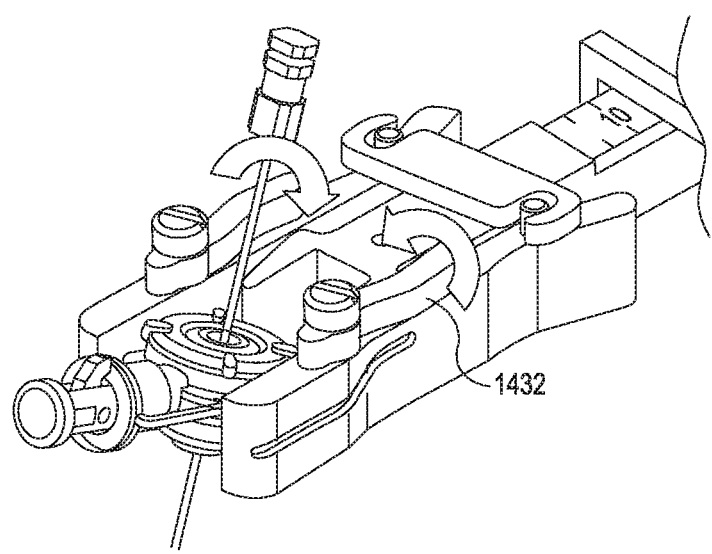

With reference to FIG. 15(d), the ball lock levers e.g. 1432 are rotated inwards or towards each other to provide a tightening force to compress the sockets e.g. 1418 against the ball joints e.g. 1416 and thus, securing the compliance device 1408 at any desired final angle.

In the example embodiment, to release the compliance device 1408, the ball lock levers e.g. 1432 can be rotated outwards or in a loosening arrangement, opening of the safety lock 1426 and a depressive force exerted on the clamp release end portions 1502, 1504. That is, the release of the compliance device 1408 is using the reverse order of the above engagement steps.

In an alternative example embodiment, the clamping mechanism may be modified to have one movable clamping finger. That is, one other clamping finger can be a fixed wall or fixed member. The movable clamping finger may be urged towards the fixed member to clamp the compliance device.

Figure 16:
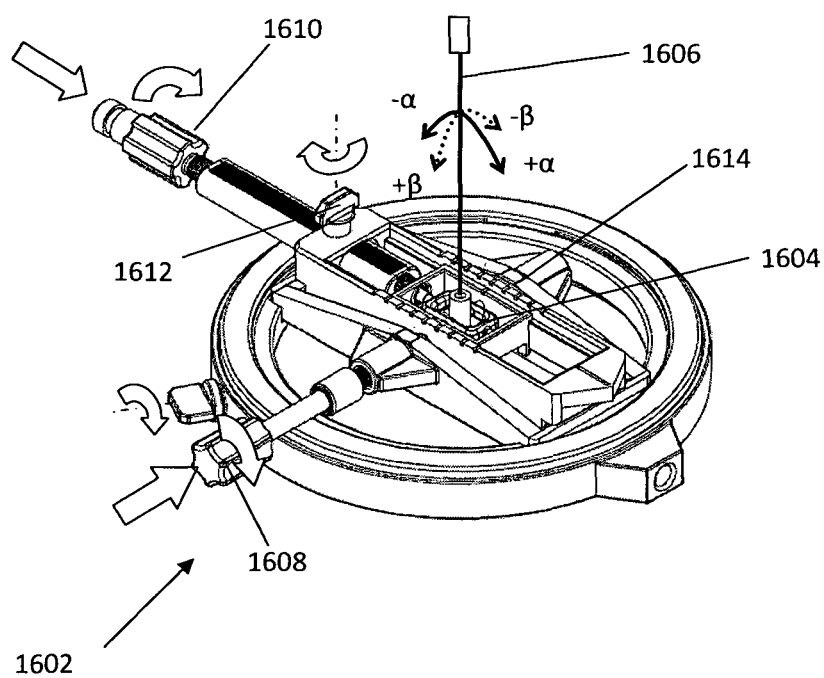
FIG. 16 is a schematic drawing for illustrating another apparatus for guiding an instrument in an example embodiment.

FIG. 16 is a schematic drawing for illustrating another apparatus for guiding an instrument in an example embodiment. The apparatus 1602 can engage or co-operate with a compliance device 1604 for guiding an instrument such as a hollow needle 1606. The apparatus 1602 comprises a y-rod 1608 provided as an actuating member/mechanism to actuate y-axis movement of the compliance device 1604, and a x-rod 1610 provided as a second actuating member/mechanism to actuate the x-axis movement of the compliance device 1604. The compliance device 1604 comprises a body having a shaft for receiving the instrument. The compliance mechanism is substantially similar to the mechanism as described with reference to FIGS. 4(b)(i) to (iii).

In the example embodiment, both fine and coarse tuning are provided for the YZ-plane movement of the needle 1606. For the XZ-plane movement of the needle 1606, fine tuning adjustment is provided. Fine tuning adjustment is provided for adjusting/changing an insertion angle of the needle 1606.

A locking mechanism/member 1612 is provided. The locking member 1612 is a screw member provided on the main body 1614 of the apparatus 1602. To lock movement of the x-rod 1610, the locking member 1612 is screwed using screw threads (not shown) of the main body 1614 and exerts a compressive force on the x-rod 1610. Thus, movement in the x-direction can be restricted, leaving only movement in the y-direction.

Figure 17:
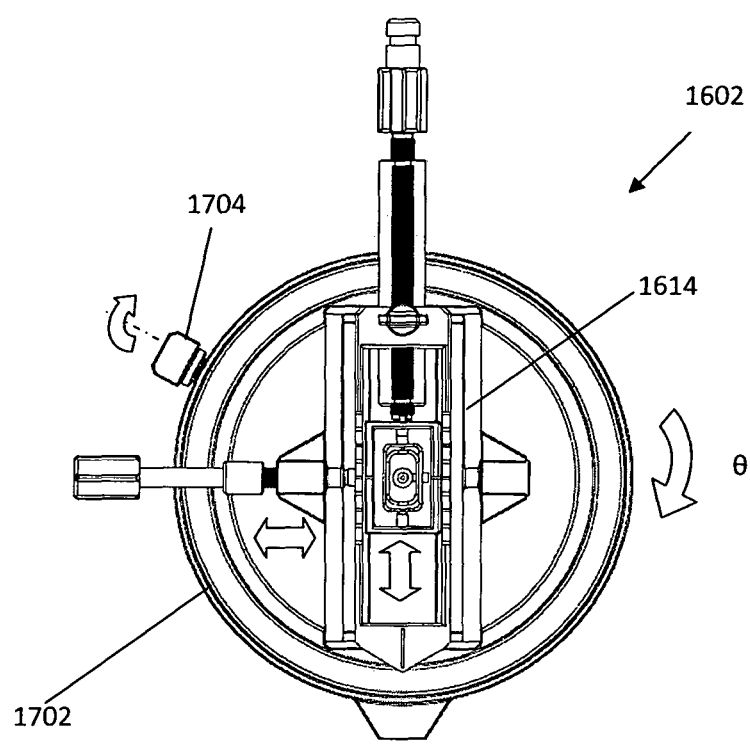
FIG. 17 is a schematic top view drawing of the apparatus of FIG. 16.
Figure 18:
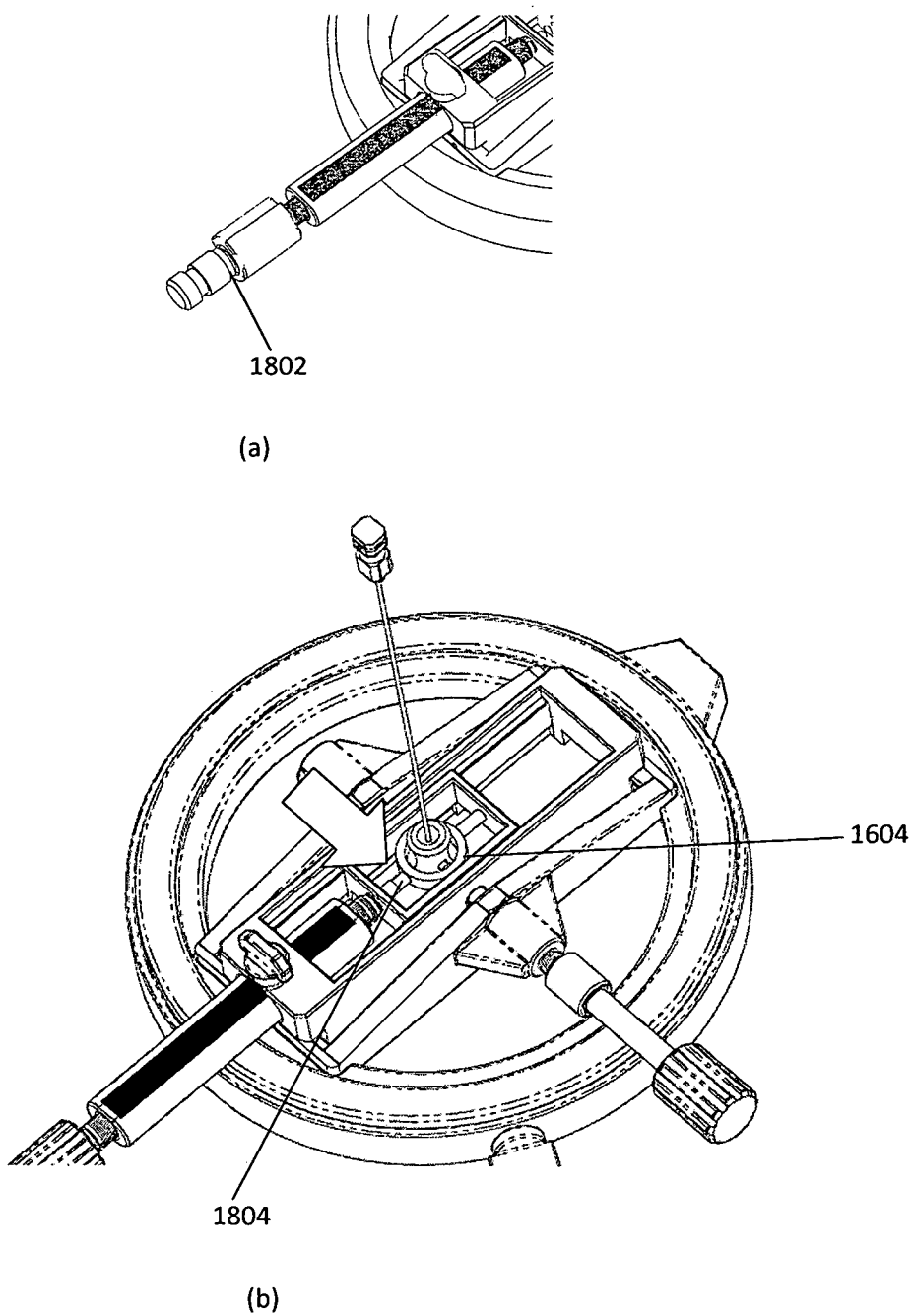
FIGS. 18(a) to (d) are schematic drawings for illustrating retention/holding and release of an instrument in an example embodiment.

FIG. 17 is a schematic top view drawing of the apparatus of FIG. 16. A rotation mechanism/member 1702 is provided as a center ring. A rotational locking member 1704 is a screw member provided on the rotation mechanism/member 1702 of the apparatus 1602. The rotational locking member 1704 can be used to restrict rotation of the main body 1614. The main body 1614 can be rotated about a 360 degree rotational angle about the z-axis or axis going into the paper. Compare theta θ. In the example embodiment, the apparatus 1602 is positioned over a subject during use. In this regard, the apparatus 1602 is preferably, either entirely or partially, constructed of material such that shadowing effects during imaging is substantially reduced and/or prevented. For example, at least a holding member of the apparatus 1602 may be constructed of such material. For example, for radioactive imaging such as x-ray imaging, the apparatus 1602 is preferably constructed of radio transparent, or radio-lucent, or radio translucent, material. Such material may include, but is not limited to, titanium, glass, polystyrene, polyurethane, PVC, polyether ether ketone (PEEK), paper etc. Thus, shadowing effects by the apparatus can be prevented on x-ray or radioactive images. This is to prevent and shadowing on the X-ray image.

In some embodiments, the compliance device 1604 is preferably substantially constructed of material such that shadowing effects during the imaging is substantially reduced and/or prevented. For example, for radioactive imaging such as x-ray imaging, the compliance device 1604 is preferably constructed of radio transparent, or radiolucent, or radio translucent, material. Such material may include, but is not limited to, titanium, glass, polystyrene, polyurethane, PVC, polyether ether ketone (PEEK), paper etc.

FIGS. 18(a) to (d) are schematic drawings for illustrating retention/holding and release of an instrument in an example embodiment.

With reference to FIG. 18(a), a plug 1802 is provided within the x-rod 1610. FIG. 18(a) shows the plug in an engaged position.

FIG. 18(b) illustrates the other end of the x-rod 1610 when the plug is in the engaged position. The compliance device 1604 is contacted by an extended holding shaft 1804 of the x-rod 1610. The holding shaft 1804 contacts a corresponding depression/hole 1806 of the compliance device 1604, thus securing/locking the compliance device 1604 in position. Thus, the holding shaft 1804 functions as a holding member of the apparatus 1602 and is coupled via the x-rod 1610 to the main body 1614.

With reference to FIG. 18(c), a force is applied to the plug 1802, e.g. by pulling the plug 1802, to move the plug 1802 into a disengaged position. The holding shaft 1804 is disengaged/retracted from the depression/hole 1806. Thus, the compliance device 1604 is released from position and may drop away from the apparatus 1602, while still maintaining the needle 1810 within a shaft (not shown) of the compliance device 1604.

With reference to FIG. 18(d), after the compliance device 1604 reaches the insertion surface of the subject, an opening 1808 is therefore available about the needle 1810. Subsequently, the apparatus 1602 can be removed by keeping the needle 1810 within the opening 1808, e.g. after releasing a locking on the apparatus 1602 by e.g. a supporting arm (compare 126 of FIG. 1(b)).

Figure 19:
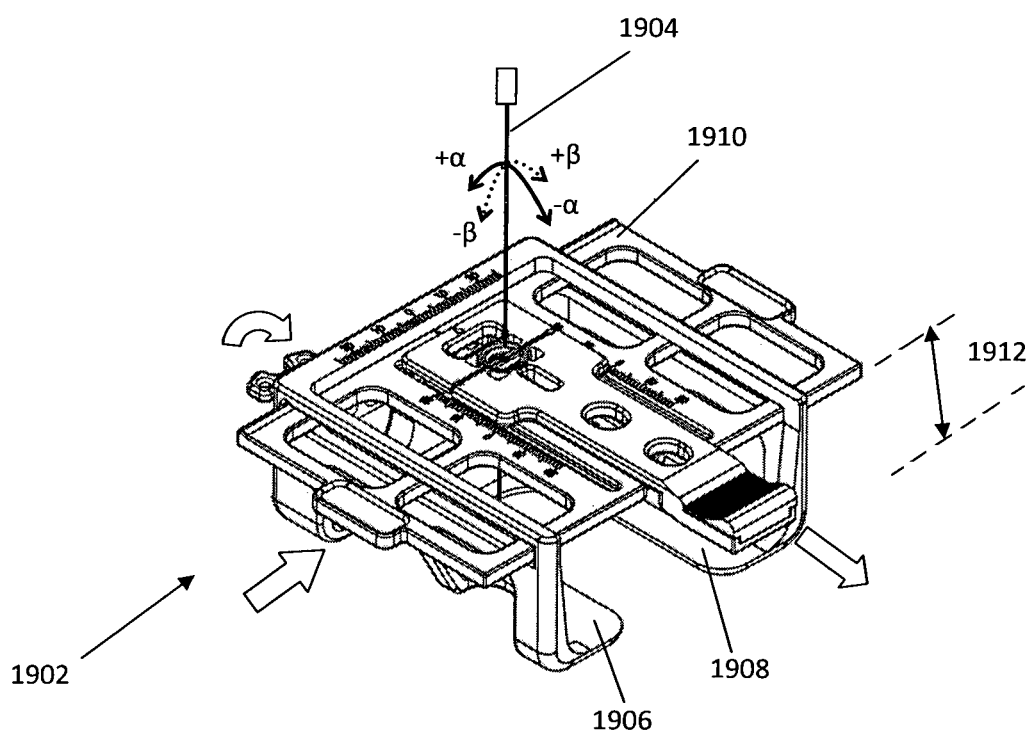
FIG. 19 is a schematic drawing for illustrating another apparatus for guiding an instrument in an example embodiment.

FIG. 19 is a schematic drawing for illustrating another apparatus for guiding an instrument in an example embodiment. The apparatus 1902 may engage an instrument such as a hollow needle 1904.

In some embodiments, the apparatus 1902 is preferably, either entirely or partially, constructed of material such that shadowing effects during imaging is substantially reduced and/or prevented. For example, at least a holding member of the apparatus 1902 may be constructed of such material. For example, for radioactive imaging such as x-ray imaging, the apparatus 1902 is preferably constructed of radio transparent, or radiolucent, or radio translucent, material. Such material may include, but is not limited to, titanium, glass, polystyrene, polyurethane, PVC, polyether ether ketone (PEEK), paper etc. Thus, shadowing effects by the apparatus can be prevented on x-ray or radioactive images. This is to prevent and shadowing on the X-ray image.

In the example embodiment, the apparatus 1902 is free of any supporting arm (compare 126 of FIG. 1(b)) and can be a dual-plane (e.g. XZ plane and YZ plane) body mount apparatus. The apparatus 1902 can be directly mounted on a subject body with a mounting base. In the example embodiment, the mounting base comprises one or more mounting segments/legs 1906, 1908 abutting the subject. To rotate the apparatus 1902, a user can hold the apparatus 1902 at the edges (e.g. of the main body) and rotate the apparatus 1902 freely. For mounting, the apparatus 1902 can be temporarily adhered to the subject by means of adhesive tape or gel applied to either the subject or the mounting base e.g. mounting segments/legs 1906, 1908. Such means of adhesive tape or gel can also function as rotation locking. Thus, a XZ-plane and YZ-plane mechanism 1910 is elevated at a constant/fixed Z-axis height (compare 1912) above and parallel to the surface for mounting.

As the apparatus 1902 can be directly mounted, the apparatus 1902 can be aligned to any angle on the surface for mounting and therefore, advantageously providing a flexibility of not being restricted by e.g. the relative position and size of an operating table/bed. Further, as the apparatus 1902 can be directly mounted on the subject, the apparatus 1902 can move in tandem with e.g. the breathing patterns and frequencies of the subject. Advantageously, the possibility of tissue and organ rupture can be minimised as the apparatus 1902 moves together with the subject.

Figure 20:
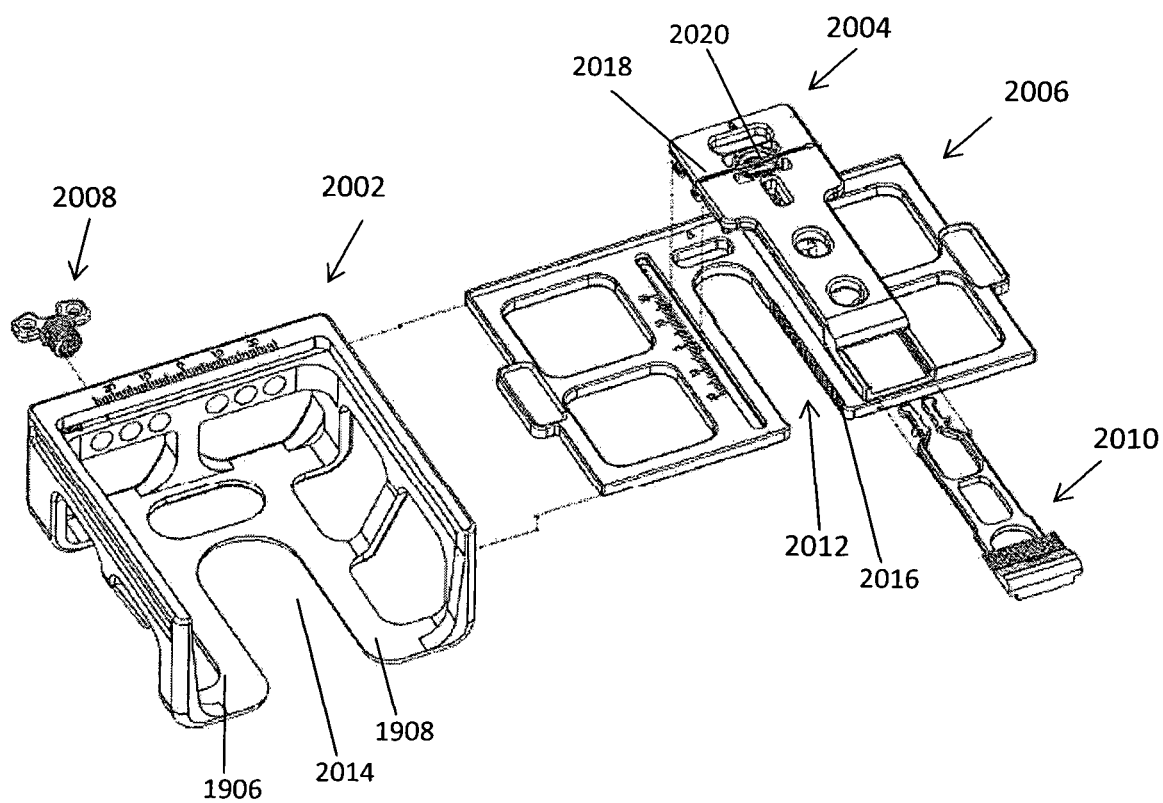
FIG. 20 is an exploded view of the apparatus of FIG. 19.
Figure 22:
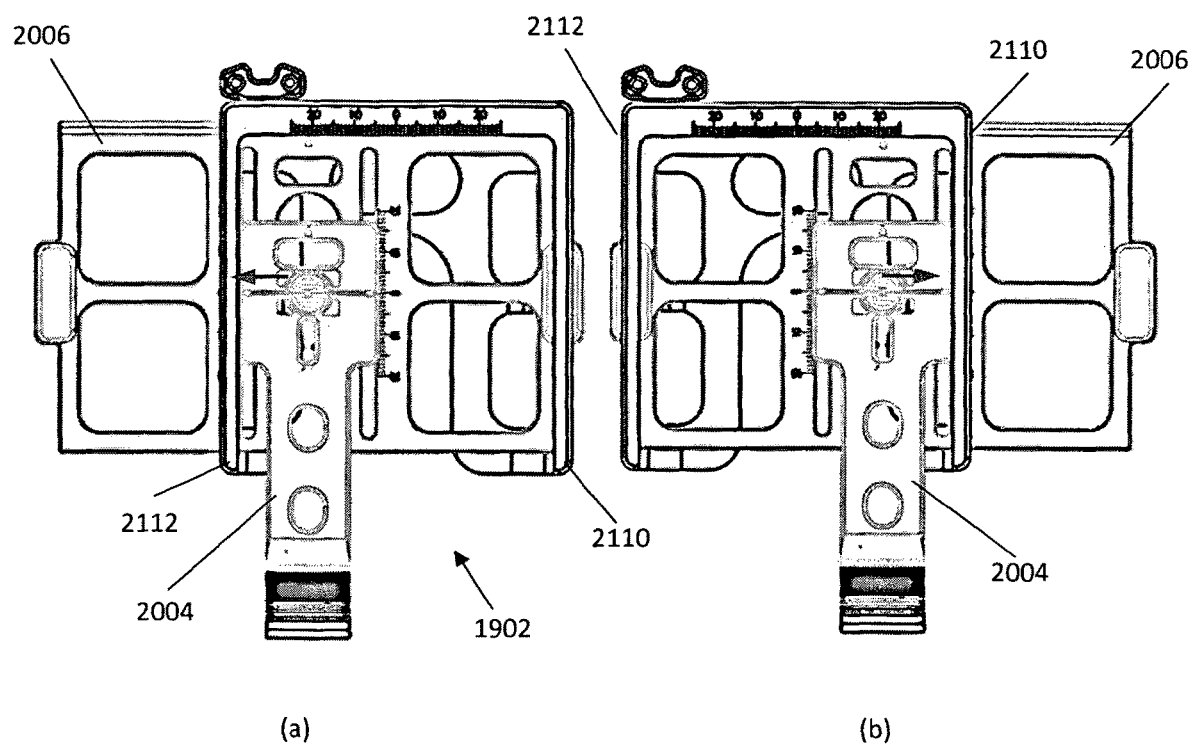
FIG. 22(a) is a schematic top view drawing of the apparatus of FIG. 19 with a second actuating mechanism/member fully extended in one x-axis direction in an example embodiment.
FIG. 22(b) is a schematic top view drawing of the apparatus of FIG. 19 with the second actuating mechanism/member fully extended in another x-axis direction in the example embodiment.

FIG. 20 is an exploded view of the apparatus 1902 of FIG. 19. With reference to FIG. 20, the apparatus 1902 comprises a main body 2002, a first actuating mechanism/member 2004, a second actuating mechanism/member 2006 and a locking member 2008. The first and second actuating mechanisms/members 2004, 2006 provide the XZ-plane and YZ-plane mechanism 1910. The main body 2002 comprises the mounting base e.g. in turn comprising mounting segments/legs 1906, 1908 for adhering to the subject. The main body 2002 also elevates the XZ-plane and YZ-plane mechanism 1910 to a fixed Z-axis height from the mounting segments/legs 1906, 1908.

The first actuating mechanism/member 2004 can be in the form of a slider for providing e.g. y-axis movement on the main body 2002. The second actuating mechanism/member 2006 can also be in the form of a slider for providing e.g. x-axis movement on the main body 2002. The first actuating mechanism/member 2004 comprises a cavity for receiving a locking latch member 2010 for locking movement or further extension in the y-axis. The locking member 2008 is provided for locking movement in the x-axis. The locking member 2008 may be a screw type member for functioning as a screw rotational lock.

The second actuating mechanism/member 2006 further comprises a travel path 2012 for an instrument, such as a needle, to be able to traverse freely. As shown, a corresponding travel path 2014 is provided at the main body 2002. The rotational movement of the instrument about a pivot point external the apparatus is preferably within the travel path 2012.

The second actuating mechanism/member 2006 further comprises serrations e.g. 2016 provided on, preferably, both walls of the travel path 2012. The serrations function to co-operate with a flexible arm (not shown) disposed within the first actuating mechanism/member 2004, the flexible arm being movable by the locking latch member 2010, for locking movement or further extension in the y-axis when desired.

An aperture 2020 is provided on the first actuating mechanism/member 2004 as a holding member for holding/retaining an instrument. The first actuating mechanism/member 2004 also comprises a pre-weakened portion/line 2018.

FIG. 21(a) is a schematic drawing of the apparatus 1902 when assembled. FIG. 21(b) is a schematic top view drawing of the apparatus 1902. For ease of description, like numerals are used to refer to similar components from FIGS. 19 and 20.

With reference to FIG. 21(a), the top surface of the first actuating mechanism/member 2004 (i.e. in the y-direction) is provided flushed with the main body 2002. That is, the top surface of the first actuating mechanism/member 2004 preferably does not protrude above the main body 2002.

With reference to FIG. 21(b), an instrument holder 2102 is provided for retaining/holding an instrument such as a hollow needle (compare 1904 of FIG. 19). The instrument holder 2102 is provided on the XZ-plane and YZ-plane mechanism 1910. A needle may be inserted through an aperture 2104 provided in the instrument holder 2102. The constant-height elevated XZ-plane and YZ-plane mechanism 1910 allows guidance of a needle tip position with the pivot point located at an insertion point on a subject or at the tip of the needle. Thus, the pivot point is external to the apparatus 1902. The resolution of the needle tip movement is based on the elevation height. The aperture 2104 allows the needle to slide freely along the plane of insertion or the insertion surface of the subject. The movement of the needle is based on the XZ- and YZ-planes motion provided by movement in the X-axis and Y-axis (compare description with reference to FIGS. 2(a) and (b)).

Movement or a combination of movements in the X-axis and Y-axis may adjust/shift the needle tip position e.g. within the subject. The second actuating mechanism/member 2006 (i.e. slider in the x-axis direction) is capable of sliding in a parallel direction relative to the main body 2002 e.g. by application of a pushing or pulling force in the x-direction on either of pads 2106, 2108.

The movement in the x-direction is constrained by the first actuating mechanism/member 2004 (i.e. slider in the y-direction) assembled on the second actuating mechanism/member 2006. That is, the second actuating mechanism/member 2006 is maintained within end walls 2110, 2112 of the main body 2002. Reference here is also made to FIGS. 22(a) and (b). FIG. 22(a) is a schematic top view drawing of the apparatus 1902 with the second actuating mechanism/member 2006 fully extended in one x-axis direction (e.g. the +x-direction). FIG. 22(b) is a schematic top view drawing of the apparatus 1902 with the second actuating mechanism/member 2006 fully extended in the other x-axis direction (e.g. the −x-direction).

Figure 23:
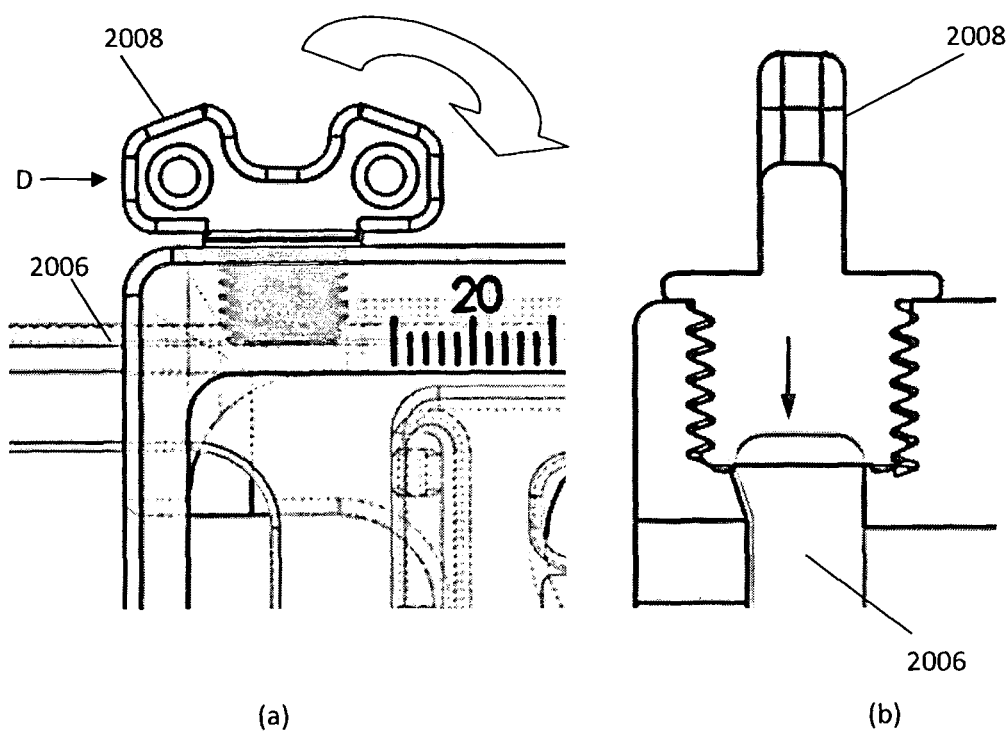
FIG. 23(a) is a schematic drawing of a locking member engaged with a second actuating mechanism/member in an example embodiment.
FIG. 23(b) is a schematic cross-sectional drawing of the locking member engaged with the second actuating mechanism/member when viewed from arrow D in the example embodiment.

Returning to FIG. 21(b), the locking member 2008 can engage the second actuating mechanism/member 2006 via screw threads (not shown) within the main body 2002. When the locking member 2008 is engaged or screwed to engage, the locking member 2008 exerts a compressive friction force on the second actuating mechanism/member 2006 against the main body 2002 to restrict movement in the x-axis direction. The locking member 2008 can restrict movement in the x-direction such that only further movement along a single axis (y-direction) is allowed. The locking member 2008 can be a screw lock nut. Reference here is also made to FIGS. 23(a) and (b). FIG. 23(a) is a schematic drawing of the locking member 2008 engaged with the second actuating mechanism/member 2006. FIG. 23(b) is a schematic cross-sectional drawing of the locking member 2008 engaged with the second actuating mechanism/member 2006 when viewed from arrow D.

Figure 24:
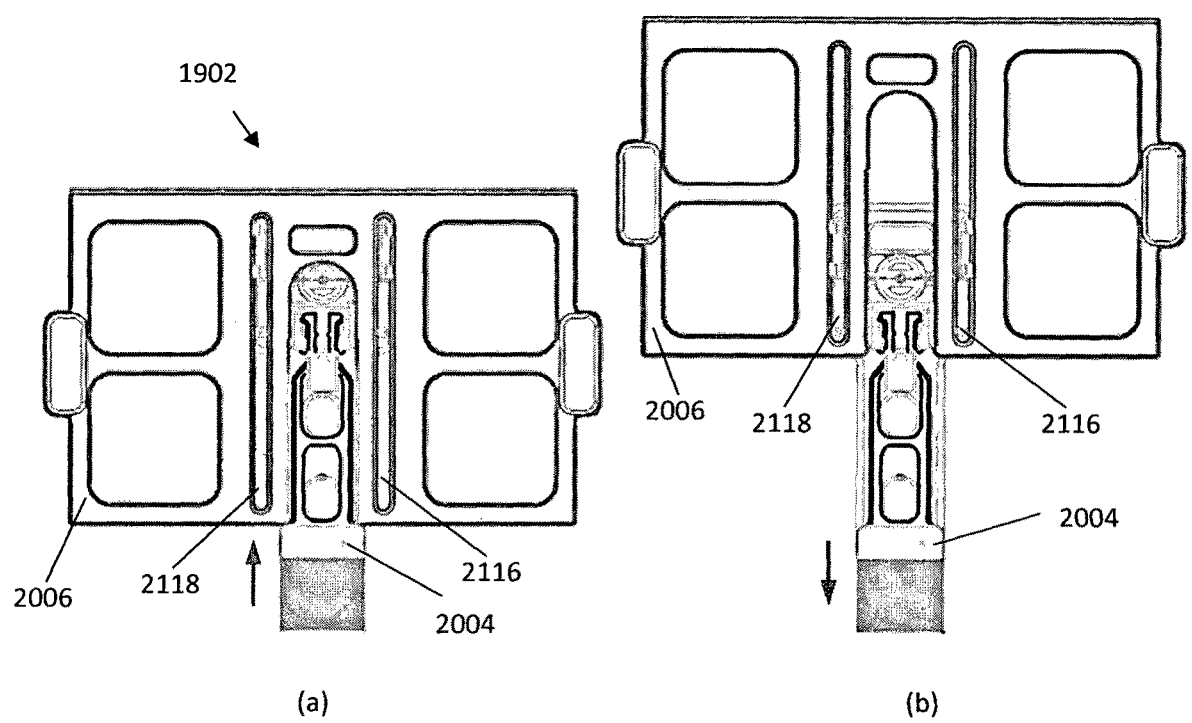
FIG. 24(a) is a schematic bottom view drawing of the apparatus of FIG. 19 with a first actuating mechanism/member fully extended in one y-axis direction in an example embodiment.
FIG. 24(b) is a schematic bottom view drawing of the apparatus of FIG. 19 with the first actuating mechanism/member fully extended in another y-axis direction in the example embodiment.

Returning to FIG. 21(b), the first actuating mechanism/member 2004 is capable of sliding in a perpendicular direction relative to the second actuating mechanism/member 2006 e.g. by application of a pushing or pulling force in the y-direction on a pad 2114 disposed on a portion of the first actuating mechanism/member 2004, the portion extended external the main body 2002. The first actuating mechanism/member 2004 travels in the y-axis direction along gliding slots 2116, 2118 provided on the second actuating mechanism/member 2006. The first actuating mechanism/member 2004 can slide along the slots 2116, 2118. The slots 2116, 2118 are close-ended as shown. The limits of movement of the first actuating mechanism/member 2004 are provided by the ends of the gliding slots 2116, 2118. Reference here is also made to FIGS. 24(a) and (b). FIG. 24(a) is a schematic bottom view drawing of the apparatus 1902 with the first actuating mechanism/member 2004 fully extended in one y-axis direction (e.g. the +y-direction). FIG. 24(b) is a schematic bottom view drawing of the apparatus 1902 with the first actuating mechanism/member 2004 fully extended in the other y-axis direction (e.g. the −y-direction).

Returning to FIG. 21(b), movement in the y-axis direction may be locked by pulling or extending the locking latch member 2010 from within the cavity of the first actuating mechanism/member 2004.

Figure 25:
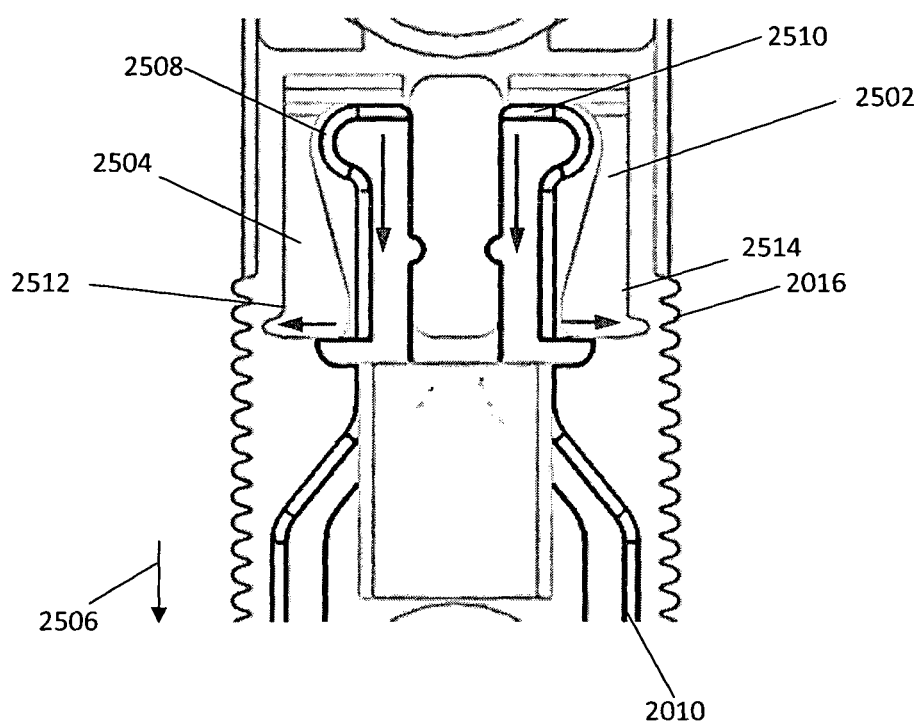
FIG. 25 is a schematic drawing for illustrating engagement of a locking latch member in an example embodiment.

FIG. 25 is a schematic drawing for illustrating engagement of the locking latch member in an example embodiment. The locking latch member 2010 is adhered to a flexible member e.g. 2502, 2504 disposed within the first actuating mechanism/member 2004. When the locking latch member 2010 is extended (compare 2506) from within the cavity of the first actuating mechanism/member (not shown), the ends 2508, 2510 of the locking latch member 2010 function to push outwards or extend portions of the flexible member e.g. 2502, 2504 as locking sub-members. The extended portions 2512, 2514 of the flexible arm e.g. 2502, 2504 or the locking sub-members may engage the serrations or gear teeth e.g. 2016 provided on the walls of the travel path (compare 2012 of FIG. 20) of the second actuating mechanism/member (not shown). The engagement can thus restrict movement along the y-axis direction.

Figure 26:
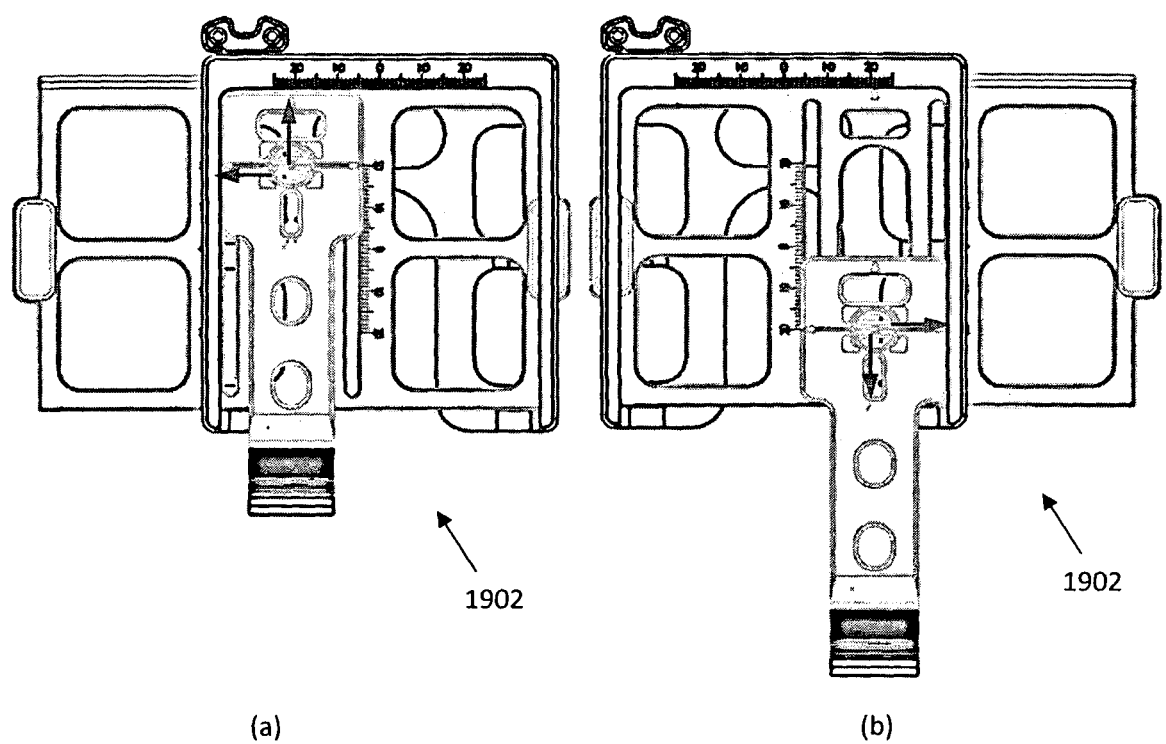
FIGS. 26(a) and (b) are schematic top view drawings of the apparatus of FIG. 19 for illustrating a range of movement in an example embodiment.

FIGS. 26(a) and (b) are schematic top view drawings of the apparatus 1902 for illustrating the range of movement in an example embodiment. FIG. 26(a) shows the apparatus 1902 fully extended in a −x-direction and +y-direction. FIG. 26(b) shows the apparatus 1902 fully extended in a +x-direction and −y-direction.

With reference to FIG. 20, a pre-weakened portion/line 2018 can be provided across the first actuating mechanism/member 2004. It will be appreciated that the pre-weakened portion can alternatively be provided on any component of the apparatus 1902, e.g. on the main body and/or the second actuating mechanism/member etc.

Figure 27:
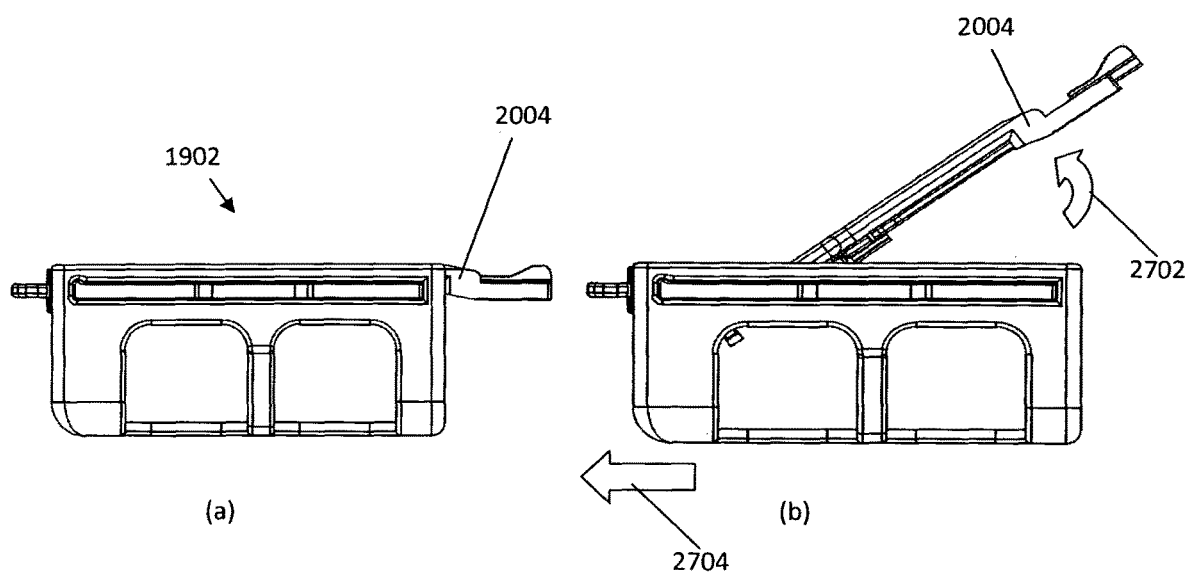
FIGS. 27(a) and (b) are schematic side view drawings of the apparatus of FIG. 19 for illustrating release of an instrument in an example embodiment.

FIGS. 27(a) and (b) are schematic side view drawings of the apparatus 1902 for illustrating release of an instrument in an example embodiment. FIG. 27(a) shows a final position of the apparatus for guiding an instrument, for example, after insertion of a needle into a subject.

With reference to FIG. 27(b), the first actuating mechanism/member 2004 is lifted (compare 2702) to break the first actuating mechanism/member 2004 along the pre-weakened portion/line (compare 2018 of FIG. 20). After the breaking, a cavity or free passage is created for the inserted needle. The mounted apparatus (compare 1902 of FIG. 19) can be removed from the needle. For example, the main body and the second actuating mechanism/member can be removed in the direction denoted by numeral 2704. Thus, instrument release can be performed without any component contacting the inserted instrument. In the example embodiment, the breaking is destructive rendering the apparatus non-reusable.

Thus, in the described example embodiments, an apparatus may be provided for translational movement of a part of an instrument or a needle such that the needle can tilt to an angle. The tilting/rotational angle may be about a pivot point that is maintained e.g. at the needle tip. The apparatus may effect translational movement of the needle in a single plane such that the needle moves in a dual-planes (e.g. XZ and YZ planes) manner that causes the needle to tilt/rotate to 2 angles within the respective planes. The apparatus can provide fine and coarse adjustments for the XZ- and YZ-planes movement. In example embodiments, the range of the XZ- and YZ-planes movement/adjustment is in a range of 0 to about 200 mm. The holding of the needle may be a toggle (e.g. using a plug) or clipping (using a clamp mechanism). In the example embodiments, the material used to construct the apparatuses may preferably be hard plastic such as polycarbonate (PC), PEEK, titanium and/or Acrylonitrile Butadiene Styrene (ABS) etc. Further, the material used to construct the apparatuses may preferably be radio-transparent or translucent material to minimise or prevent shadowing in the x-ray images.

In some example embodiments, a laser source may be mounted on a C-arm receiver and away from the x-ray imaging. The laser beam (by a prism) may be perpendicular to the C-arm receiver plane. The laser may be directed to the subject using the prism. The visible reference or point of the laser may be adjustable using a movable mechanism mounted on the C-arm receiver.

In the described example embodiments, having a pivot point external of the apparatus for guiding an instrument may provide certainties over other apparatus that allow free rotation of the instrument, e.g. the point of rotation may be within the main body of such apparatus. It has been recognised by the inventors that providing too many freedom of rotation or motion may result in inaccuracies during procedures. Further, the apparatus in example embodiments may be relatively cheaper and simple to use as compared to robotic devices. In addition, the apparatus in example embodiments may allow a user to have tactile feedback directly during insertion of the instrument. In addition, if there are any deviations due to subject movement e.g. respiration, the instrument may be guided back to path using the apparatus in example embodiments. Further, the system and apparatus in example embodiments may reduce x-ray exposure during the procedure as the x-ray may be switched off during needle guidance/insertion. In addition, it has been recognised by the inventors that the apparatus in example embodiments may also simplify techniques so that the learning curve for the procedures may be shortened for new users. It has also been recognised that due to easier guidance and referencing, a shorter time for procedures may be obtained.

Therefore, the example embodiments may advantageously provide a passive PAK assist device (PAK-AD) that may combine precision adjustment and guiding technology with the skill and dexterity of a user to manage the needle alignment and insertion process. The apparatus in example embodiments may provide that the needle be referenced for adjustment within a plane without affecting the alignment in other planes. The apparatus in example embodiments may enable a needle to be physically locked in position and allow only one DOF for insertion of the needle into a subject. The example embodiments may also provide an articulated support arm coupled with a number of guiding and locking modules to assist in achieving high alignment accuracy of the needle with respect to a target, while still providing full control to a user to adjust and insert the needle onto the target.

In the described example embodiments, although the x-axis and y-axis have been described, it will be appreciated that the example embodiments are not limited as such. For example, the x-axis and y-axis are arbitrary and can be interchangeable. In addition, other axis, even non-perpendicular axis, may be used: Similarly, although the XZ and YZ planes have been described, other planes may be used.

In addition, in the described example embodiments, the instrument such as a needle is described for ease of illustration. It will be appreciated that the apparatus and system may be provided independent of the instrument.

Furthermore, it will be appreciated that the XZ- and YZ-planes movement resulting in tilting/rotational movement about a pivot point external the apparatus of example embodiments is not limited to be used in only PAK procedures. The apparatus of example embodiments may be used for different bio-systems and other procedures such as kidney stone removal procedures, procedures for the colon, stomach, lungs etc. The apparatus of example embodiments may also be used for cosmetic procedures. The apparatus of example embodiments may be also used for non-surgical procedures that utilise guiding of instruments with respect to embedded targets, preferably with the aid of an imaging system such as X-ray imaging etc.

Further, it will be appreciated that example embodiments described having compliance devices co-operating with holding members are not limited as such. That is, these example embodiments may be modified such that the holding members directly retain/hold an instrument, i.e. without a separate compliance device.

In described example embodiments, the subject may be a human or animal subject. The target may be tissue, growth, stones etc.

Further, it will be appreciated that example embodiments may be modified such that imaging and/or alignment steps may be implemented or assisted by automated systems. That is, example embodiments may be modified to provide a partially passive. PAK-assist device, and such example embodiments are not limited to solely passive PAK-assist devices.

It will be appreciated by a person skilled in the art that other variations and/or modifications may be made to the specific embodiments without departing from the scope of the invention as broadly described. The present embodiments are, therefore, to be considered in all respects to be illustrative and not restrictive.

The invention claimed is:

1. An apparatus for guiding an instrument, the apparatus comprising,
  a main body;
  a holding member defining an aperture through which an instrument is inserted, the holding member coupled to the main body; and
  one or more actuating members that cause movement of the holding member when actuated, the movement of the holding member comprising one or more translational movements confined within a single plane that is parallel to a plane horizontal with respect to the main body and such that said confined translational movements of the holding member imparts translational movement of the aperture in the same direction as the one or more translational movements of the holding member so as to impart rotational movement of the instrument in one or more planes perpendicular to said plane that is parallel to a plane horizontal with respect to the main body, said rotational movement being about a pivot point external to the apparatus.

2. The apparatus as claimed in claim 1, wherein each actuating member is provided for effecting the translational movement of the holding member along a respective axis within said plane that is parallel to a plane horizontal with respect to the main body.

3. The apparatus as claimed in claim 1, wherein the one or more actuating members comprises a rotary screw thread member for effecting by hand said one or more translational movements of the holding member through a rotational movement of the rotary screw thread member.

4. The apparatus as claimed in claim 1, further comprising an extendable member coupled to the main body, the extendable member capable of offsetting parallel to a plane horizontal with respect to the main body a position of the holding member from the main body.

5. The apparatus as claimed in claim 4, wherein the holding member comprises at least one clamping finger being urged towards another clamping finger.

6. The apparatus as claimed in claim 5, wherein the at least one clamping finger comprises an end portion for a force to be applied to, for release of the instrument from the apparatus.

7. The apparatus as claimed in claim 5, further comprising a lock member for engaging the clamping fingers to restrict movement of the at least one clamping finger.

8. The apparatus as claimed in claim 4, wherein the holding member is configured to co-operate with a compliance device, said compliance device capable of holding the instrument in said one or more planes perpendicular to said plane that is parallel to a plane horizontal with respect to the main body.

9. The apparatus as claimed in claim 8, wherein the compliance device comprises two or more spherical joints that allow the compliance device to be compliant to movement along two perpendicular axes, and the compliance device further comprises a plunger assembly for restricting movement of the instrument in said one or more planes perpendicular to said plane that is parallel to a plane horizontal with respect to the main body.

10. The apparatus as claimed in claim 9, wherein the compliance device is capable of being individually locked in movement along each axis while allowing guidance of the instrument within said one or more planes perpendicular to said plane that is parallel to a plane horizontal with respect to the main body.

11. The apparatus as claimed in claim 8, wherein the compliance device is constructed of a material to substantially prevent shadowing effects of the compliance device in an imaging procedure.

12. The apparatus as claimed in claim 11, wherein the material is at least one selected from the group consisting of glass, polystyrene, polyurethane, PVC, polyether ether ketone (PEEK) and paper.

13. The apparatus as claimed in claim 4, wherein the apparatus is configured to release the instrument in two steps or less.

14. The apparatus as claimed in claim 1, wherein the holding member comprises an extendable shaft.

15. The apparatus as claimed in claim 14, wherein the holding member is configured to co-operate with a compliance device, said compliance device capable of holding the instrument in said one or more planes perpendicular to said plane that is parallel to a plane horizontal with respect to the main body.

16. The apparatus as claimed in claim 15, wherein the compliance device is configured to be contacted by at least two rounded walls provided on the main body of the apparatus that allow the compliance device to be compliant to movement along at least one axis within said plane that is parallel to a plane horizontal with respect to the main body.

17. The apparatus as claimed in claim 15, wherein the holding member further comprises a plug that is capable of actuating the extendable shaft for engagement with the compliance device, the extending or retracting of the shaft for maintaining the compliance device in relation to the main body or for release of the compliance device from the main body.

18. The apparatus as claimed in claim 15, wherein the compliance device is constructed of a material to substantially prevent shadowing effects of the compliance device in an imaging procedure.

19. The apparatus as claimed in claim 18, wherein the material is at least one selected from the group consisting of glass, polystyrene, polyurethane, PVC, polyether ether ketone (PEEK) and paper.

20. The apparatus as claimed in claim 1, further comprising a mounting base disposed on the main body, the mounting base for contacting a subject surface such that the holding member is disposed at a fixed distance in parallel to the subject surface.

21. The apparatus as claimed in claim 20, wherein the mounting base comprises two or more mounting segments for contacting the subject surface.

22. The apparatus as claimed in claim 20, wherein a first actuating member comprises one or more guiding slots and a second actuating member is capable of moving in relation to the first actuating member via the guiding slots within the single plane that is parallel to a plane horizontal with respect to the main body, and parallel to the subject surface.

23. The apparatus as claimed in claim 22, wherein the first actuating member further comprises a travel path such that said providing rotational movement of an instrument about a pivot point external the apparatus and in said one or more planes perpendicular to said plane that is parallel to a plane horizontal with respect to the main body is within the travel path.

24. The apparatus as claimed in claim 23, further comprising a locking latch member that is capable of causing extension of one or more locking sub-members to engage one or more walls of the travel path, to restrict movement of the holding member in relation to the travel path.

25. The apparatus as claimed in claim 20, wherein at least one actuating member is provided with a pre-determined weakened portion such that said at least one actuating member is breakable for releasing an instrument from the holding member.

26. The apparatus as claimed in claim 20, wherein the one or more actuating members comprises a hand-operable slider mechanism.

27. The apparatus as claimed in claim 1, further comprising a rotation member coupled to the main body for effecting rotation of the main body about a vertical axis passing through a center of the main body.

28. The apparatus as claimed in claim 27, further comprising a rotational locking member for restricting rotation of the main body.

29. The apparatus as claimed in claim 1, further comprising a locking member capable of restricting translational movement of the holding member in one axis within the single plane that is parallel to a plane horizontal with respect to the main body such that only further movement of the holding member along a single axis within the single plane that is parallel to a plane horizontal with respect to the main body is allowed.

30. The apparatus as claimed in claim 1, wherein at least the holding member is constructed of a material to substantially prevent shadowing effects of the holding member in an imaging procedure.

31. The apparatus as claimed in claim 30, wherein the material is at least one selected from the group consisting of glass, polystyrene, polyurethane, PVC, polyether ether ketone (PEEK) and paper.

32. A method for guiding an instrument, the method comprising,
holding an instrument in an aperture of a holding member;
providing a pivot point external to the holding member;
actuating one or more actuating members of the apparatus to move the aperture with one or more translational movements confined within a single plane that is parallel to a plane horizontal with respect to a main body of the apparatus, the aperture moving in the same direction as the one or more translational movements so as to impart rotational movement of the instrument confined within one or more planes perpendicular to said plane that is parallel to a plane horizontal with respect to the main body, said rotational movement of the instrument being about the pivot point external to the holding member.

33. The method as claimed in claim 32, wherein for the step of actuating one or more actuating members to move the holding member, the method further comprises effecting the translational movement of the holding member along a respective axis parallel to the translation direction of each actuating member and within said plane that is parallel to a plane horizontal with respect to the main body.

34. The method as claimed in claim 32, further comprising providing a rotary screw thread member as the one or more actuating members, and effecting by hand said one or more translational movements of the holding member through a rotational movement of the rotary screw thread member.

35. The method as claimed in claim 32, further comprising providing a mounting base coupled to the holding member, and contacting a surface of a subject such that the holding member is disposed at a fixed distance in parallel to the surface of the subject.

36. The method as claimed in claim 35, wherein the mounting base comprises two or more mounting segments for contacting the surface of the subject.

37. The method as claimed in claim 35, further comprising providing a hand-operable slider mechanism as the actuating member, and effecting by hand the movement of the holding member through a movement of the hand-operable slider mechanism.

38. An apparatus for guiding an instrument, the apparatus comprising,
a main body;
a holding member defining an aperture through which an instrument is inserted, the holding member coupled to the main body and comprising an extendable shaft and a plug capable of actuating the extendable shaft for engagement with a compliance device, wherein extension and retraction of the extendable shaft maintains the compliance device in relation to the main body or releases the compliance device from the main body; and
one or more actuating members that cause movement of the holding member when actuated, the movement of the holding member comprising one or more translational movements confined within a single plane that is parallel to a plane horizontal with respect to the main body and such that said confined translational movements of the holding member are capable of moving an instrument in the same direction as the one or more translational movements so as to provide rotational movement of the instrument in one or more planes perpendicular to said plane that is parallel to a plane horizontal with respect to the main body, said rotational movement being about a pivot point external the apparatus, wherein the compliance device is capable of holding the instrument in said one or more planes perpendicular to said plane that is parallel to a plane horizontal with respect to the main body.

* * * * *